(12) United States Patent
Hakonarson et al.

(10) Patent No.: US 11,219,617 B2
(45) Date of Patent: Jan. 11, 2022

(54) METHODS OF DIAGNOSING AND TREATING AUTISM

(71) Applicant: THE CHILDREN'S HOSPITAL OF PHILADELPHIA, Philadelphia, PA (US)

(72) Inventors: Hakon Hakonarson, Malvern, PA (US); Tara Wenger, Seattle, WA (US); Charlly Kao, Philadelphia, PA (US); Dexter Hadley, Philadelphia, PA (US); Zhi-liang Wu, North Potomac, MD (US); Joseph Glessner, Mullica Hill, NJ (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 1060 days.

(21) Appl. No.: 14/740,230

(22) Filed: Jun. 15, 2015

(65) Prior Publication Data
US 2017/0083664 A1    Mar. 23, 2017

Related U.S. Application Data

(63) Continuation-in-part of application No. 14/292,480, filed on May 30, 2014.

(51) Int. Cl.
| | | |
|---|---|---|
| *C12Q 1/68* | (2018.01) | |
| *C12P 19/34* | (2006.01) | |
| *A61K 31/454* | (2006.01) | |
| *G16B 20/00* | (2019.01) | |
| *C12Q 1/6883* | (2018.01) | |

(52) U.S. Cl.
CPC .......... *A61K 31/454* (2013.01); *C12Q 1/6883* (2013.01); *G16B 20/00* (2019.02); *C12Q 2600/118* (2013.01); *C12Q 2600/156* (2013.01)

(58) Field of Classification Search
CPC .................. C12Q 1/6883; C12Q 2600/156
See application file for complete search history.

(56) References Cited

U.S. PATENT DOCUMENTS

| | | |
|---|---|---|
| 2002/0035068 A1 | 3/2002 | Van Kammen |
| 2002/0142305 A1 | 10/2002 | Chin et al. |
| 2003/0040089 A1 | 2/2003 | Legrain et al. |
| 2003/0092019 A1 | 5/2003 | Meyer et al. |
| 2004/0116505 A1 | 6/2004 | Krauss et al. |
| 2005/0233321 A1 | 10/2005 | Hess et al. |
| 2007/0244152 A1 | 10/2007 | Lowy |
| 2007/0292962 A1 | 12/2007 | Pericak-Vance et al. |
| 2007/0299113 A1 | 12/2007 | Kalvinsh et al. |
| 2009/0176740 A1 | 7/2009 | Phillips, II |
| 2010/0120628 A1 | 5/2010 | Belouchi et al. |
| 2010/0143921 A1 | 6/2010 | Sadee et al. |
| 2010/0216734 A1 | 8/2010 | Barlow et al. |
| 2011/0046090 A1 | 2/2011 | Barlow et al. |
| 2011/0269688 A1 | 11/2011 | Hakonarson et al. |
| 2012/0149677 A1 | 6/2012 | Dudkin et al. |
| 2013/0143867 A1 | 6/2013 | Fogel et al. |
| 2013/0203814 A1 | 8/2013 | Glessner et al. |
| 2013/0225623 A1 | 8/2013 | Buxbaum et al. |
| 2014/0303243 A1 | 10/2014 | Hakonarson et al. |
| 2016/0032390 A1 | 2/2016 | Hakonarson et al. |

FOREIGN PATENT DOCUMENTS

| | | |
|---|---|---|
| WO | 2003056167 A2 | 7/2003 |
| WO | 2005094801 A1 | 10/2005 |
| WO | 2007/104035 A1 | 9/2007 |
| WO | 2008136995 A1 | 11/2008 |
| WO | 2009105718 A1 | 8/2009 |
| WO | 2013006857 A1 | 1/2010 |
| WO | 2010057112 A2 | 5/2010 |
| WO | 2016/022324 A1 | 2/2016 |

OTHER PUBLICATIONS

Childress, A. et al. Expert Opinion on Investigational Drugs, 2016, vol. 25, No. 4, 463-474 (Year: 2016).*
Karayiorgou, M. et al. Nature Reviews—Neuroscience, vol. 11, June, p. 402-416 (Year: 2010).*
Cai, Q. et al. "Multiplex ligation-dependent probe amplification for genetic screening in autism spectrum disorders: Efficient identification of known microduplications and identification of a novel microduplication in ASMT" BMC Medical Genomics vol. 1, Article No. 50 (Year: 2008).*
UCSC Genome Browser on Human Feb. 2009 (GRCh37/hg19) Assembly, gene location of RANBP1: chr22:19227275-20171251, printed from https://genome.ucsc.edu/ (Year: 2021).*
Written Opinion issued in the related Singaporean Application No. 11201609832X, dated Aug. 22, 2017.
International Search Report issued in the Application No. PCT/US2015/42354, dated Nov. 3, 2015.
International Search Report/Written Opinion issued in the related PCT/US2016/50559, filed Sep. 7, 2016.
Malykh Andrei G et al: "Piracetam and piracetam-like drugs: from basic science to novel clinical applications to CNS disorders", Drugs, Adis International Ltd, NZ, vol. 70, No. 3, Jan. 1, 2010, pp. 287-312.
J. Tarver et al: "Attention-deficit hyperactivity disorder (ADHD): an updated review of the essential facts", Child: Care, Heal th and Development, vol. 40, No. 6, Apr. 14, 2014, pp. 762-774.
Addington, et al. "Annual Research Review: Impact of advances in genetics in understanding developmental psychopathology" Journal of Child Psychology and Psychiatry 53(5): 510-518 (2009).
Akhundian, "Effect of Piracetam on attention deficit and hyperactivity disorder" Iranian Journal of Pediatrics. 2001. 11(2): 32-36 (Abstract).

(Continued)

*Primary Examiner* — Stephen T Kapushoc
(74) *Attorney, Agent, or Firm* — Kathleen D. Rigaut; Howson & Howson LLP

(57) ABSTRACT

Methods for diagnosing and treating autism spectral disorders are encompassed. In one embodiment, a patient is diagnosed as having autism spectral disorder if at least one CNV in an mGluR network gene is found in a patient sample. Patients with at least one mGluR network gene CNV are effectively treated with (+)-5-oxo-Dprolinepiperidinamide monohydrate (NS-105).

5 Claims, 27 Drawing Sheets
(5 of 27 Drawing Sheet(s) Filed in Color)

(56) References Cited

OTHER PUBLICATIONS

Baum, et al, "A Genome-Wide Association Study Implicates Diacylglycerol Kinase eta (DGKH) and Several Other Genes in the Etiology of Bipolar Disorder," Molecular Psychiatry, 13,197-207, 2008.
Benner, et al., "Evolution, Language and Analogy in Functional Genomics," Trends in Genetics,17(7), 414-418, 2001.
Bucan, Maja "Novel Approaches in Psychiatric Genomics" International Workshop on Algorithms in Bioinformatics, vol. 4645, p. 371, 2007.
Clark, et al. "Tourelle Syndrome and Klippel-Feil Anomaly in a Child with Chromosome 22q11 Duplication" Case Reports in Medicine vol. ID 361518 pp. 1-5 (2009).
Database Geo [on line] NCBI, "Illumina HumanHap550 Genotyping Beadchip v1," Feb. 5, 2008.
Elia, J. et al. "Genome-wide copy number variation study associates metabotropic glutamate receptor gene netwarks with attention deficit hyperactivity disorder" Nat Genet., 44(1):78-84, 2015.
Elia, J. et al., "Rare Structural Variants Found in Attention-Deficit Hyperactivity Disorder are Preferentially Associated with Neurodevelopmental Genes," Molecular Psychiatry, 15(6): 637-646, and supplementary table s1 (p. 1-7), 2010.
Extended European Search Report in copending European Patent Application No. 11820610.1, dated Jan. 2, 2014.
Forero, D. et al., "Candidate Genes Involved in Neural Plasticity and the Risk for Attention-Deficit Hyperactivity Disorder: a Meta-Analysis of 8 Common Variants," Journal of Psychiatry and Neuroscience, 34(5): 361-366, 2009.
Hirouch I, Masaaki, "Role of metabotropic glutamate receptor subclasses in modulation of adenylyl cyclase activity by a nootropic NS-105" European Journal of Pharmacology 387: 9-17, 2000.
Hirschhorn, et al., "A Comprehensive Review of Genetic Association Studies," Genetics in Medicine, 4(2): 45-61, 2002.
Hodgins, et al., "Adolescents with conduct disorder: does anxiety make a difference?" The J. of Forensic Psychiatric and Psychology, 22(5), 669-691, 2011.
Ioannidis, et al, "Replication Validity of Genetic Association Studies," Nature Genetics, 29, 306-309, 2001.
Jones, G. et al., "Exploratory dose-escalation study of NFC-1 in ADHD adolescents with glutamatergic gene network variants.", 62nd Annual Meeting. AACAP, Oct. 2015.
Kleefstra, T. et al. Loss-of Functions Mutations in Euchromatin Histone Methyl Transferase 1 (EHMT1) Cause the 9q34 Subtelomeric Deletion Syndrome The American Journal of Human Genetics , 79, 370-377, 2006.
Krom, M. et al., "A Common Variant in DRD3 Receptor is Associated with Autism Spectrum Disorder," Biological Psychiatry, 65(7): 625-630, 2009.
Lachman, H., et al. "Increase in GSK3β Gene Copy Number Variation in Bipolar Disorder" American Journal of Medical Genetics Part B Neuropsychiatric Genetics, 144B, 259-265, 2007.
Lesch, K-P. et al., "Genome-wide copy number variation analysis in attention-deficit/hyperactivity disorder: association with neuropeptide Y gene dosage in an extended pedigree", Molecular Psychiatry, (Published online) 16, 491-503, 2010.
Lucentini, J., "Gene Association Studies Typically Wrong," The Scientist, 20, 18(24) 2004.
Manolio, et al., "New Models of Collaboration in Genome-Wide Association Studies: The Genetic Association Information Network," Nature Genetics, 39,1045-1051, 2007.
May, et al, "How Many Species are There on Earth?" Science, 241: p. 1441, 1988.
Miller, Caroline, "How Anxiety Leads to Disruptive Behavior: kids who seem oppositional are often severely anxious" Child Mind Institute: Anxiety and Disruptive Behavior in Children, 1-3.
Moon, H., et al., "Identificaiton of DNA copy-number aberrations by array-comparative genomic hybridization in patients with schizophrenia" Biochemical and Biophysical Research Communications 344: 531-539, 2006.
Neale, B. et al., "Genome-Wide Association Scan of Attention Deficit Hyperactivity Disorder," American Journal of Medical Genetics Part B: Neuropsychiatric Genetics, 147B, 1337-1344, 2008.
O'Connor, et al., "Metabotropic Glutamate Receptor 7: At the Interface of Cognition and Emotion," Eur J Pharacol, 639, 123-131 [Abstract], 2010.
Peiffer, D., et al. High-resolution genomic profiling of chromosomal aberrations using Infinium whole-genome genotyping Genome Research ,16,1136-1148, 2006.
Rafiq, M., et al. "Mutations in the Alpha 1,2-Mannosidase Gene, MAN1B1, Cause Autosomal-Recessive Intellectual Disability" The American Journal of Human Genetics, 89,176-182, 20.
Semenova, et al., The Effects of the mGluR5 Antagonist MPRP and the mGluR2/3 Antagonist L Y341495 on Rats' Performance in the 5-choice Serial Reaction Time Task, Neuropharmacology, 52(3):863-872 [Abstract], 2007.
Stallings, M., et al. "A Genome-Wide Search for Quantitative Trait Loci That Influence Antisocial Drug Dependence in Adolescence" "Arch Gen Psychiatry", 62,1042-1051, 2005.
Stefansson, et al., "Large Recurrent Microdeletions Associated with Schizophrenia," Nature, 455 (7210), 232-236, 2008.
Stergiakouli, et al. "Fitting the pieces together: current research on the genetic basis of attention-deficit/hyperactivity disorder (ADHD)", Neuropsychiatric Disease and Treatment, 6, 551-560, 2010.
Walsh, et al., "Rare Structural Variants Disrupt Multiple Genes in Neurodevelopmental Pathways in Schizophrenia," Science, 320(5875), 539-543, 2008.
Williams, et al., "Is COMT a Susceptibility Gene for Schizophrenia?" Schizophr Bull., 33(3), 635-641, 2007.
Xu, et al., "Strong Association of de novo Copy Number Mutations with Sporadic Schizophrenia," Nat. Genet., 40 (7), 880-885, 2008.
International Search Report for PCT/US2011/048993, dated Jan. 27, 2012.
AEVI Genomic Medicine Announces Top-Line Results from Placebo-Controlled ASCEND Trial (Parts A & B) in Children with ADHD, News Release, Unlocking the potential of genomic medicine, Jan. 2, 2019.
Bloch, Michael et al., "Recent Advances in Tourette Syndrome", Curr. Opin. Neurol., 24(2): 119-125 (2011).
Dietrich, Andrea et al., "The Tourette Internatiuonal Collaborative Genetics (TIC Genetics) study, finding the genes causing Tourette syndrome: objectives and methods", Eur. Child Adolesc. Psychiatry, 24: 141-151 (2015).
Ghelardini, C. et al., "DM235 (sunifiram): a novel nootropic with potential as a cognitive enhancer", Naunyn-Schmiedeberg's Arch. Pharmacol., 365: 419-426 (2002).
Gregory, Karen J. et al., "Pharmacology of Metabotropic Glutamate Receptor Allosteric Modulators: Structural Basis and Therapeutic Potential for CNS Disorders", Progress in Molecular Biology and Translational Science, Oligomerization and Allosteric Modulation in G-Protein Coupled Receptors, edited by Terry Kenakin, vol. 115 (2013).
Kendler, Kenneth S. et al., "Familial Influences on Conduct Disorder Reflect 2 Genetic Factors and 1 Shared Environmental Factor", JAMA Psychiatry, 70(1): 78-86 (2013).
Niswender, Colleen M., "Metabotropic Glutamate Receptors: Psyciology, Pharmacology, and Disease", Annu. Rev. Pharmacol Toxicol., 50: 295-322 (2010).
Oka, Michiko et al., "A novel congnition enhancer NS-105 modulates adenylates cyclase activity through metabotropic glutamate", Arch. Pharmacol., 356: 189-196 (1997).
Childress, Ann et al., "Current Investigational Drugs for the Treatment of Attention-Deficit/Hyperactivity Disorder", Expert Opinion on Investigational Drugs, 25(4): 463-474 (2016).
Cooper, Gregory M. et al., "Systematic assessment of copy number variant detection via genome-wide SNP genotyping", Nature Genetics, 40(10): 1199—(2008).
Elia, Josephine et al., "Fasoracetam in adolescents with ADHD and glutamatergic gene network variants disrupting mGluR neurotransmitter signaling", Nature Communications, 9: 4 (2018).
Fewtrell, M.S. et al., "Hirschsprung's disease associated with a deletion of chromosome 10 (q11.2q21.2): a further ink with the neurocristophaties?", J. Med. Genet., 31: 325-327 (1994).

(56) References Cited

OTHER PUBLICATIONS

Jarrett, Matthew A. et al., "A conceptual review of the comorbidity of attention-deficit/hyperactivity disorder and anxiety: Implications for future research and practice", Clinical Psychology Review, 28: 1266-1280 (2008).
Karayiorgou, Maria et al., "22q11.2 microdeletions: linking DNA structural variation to brain dysfunction and schizophrenia", Nature, 11: 402-416 (2010).
Lo-Castro, Adriana et al., "ADHD and genetic syndromes", Brain & Development, 33: 456-461 (2011).
Palucha, Agnieszka et al., "Metabotrpic glutamate receptor ligands as possible anxiolytic and antidepressant drugs", Pharmacology & Therapeutics, 115: 116-147 (2007).
Rizzo, Renata et al., "Clinical Pharmacology of Comorbid Attention Deficit Hyperactivity Disorder in Tourette Syndrome", International Review of Neurobiology, 112: 415-444 (2013).
Shimidzu, Takako et al., "Effect of a novel cognition enhancer NS-105 on learned helplessness in rats: Possible involvement of GABAB receptor up-regulation after repeated treatment", European Journal of Pharmacology, 338: 225-232 (1997).
Turgay, Atilla, "Treatment of Comorbidity in Conduct Disorder with Attention Deficit Hyperactivity (ADHD)", Essential Psychopharmacology, 6(5): 277-290 (2005).
US National Library of Medicine, "Phase I Single Dose, Open-Label Pharmacokinetic Study and Single-Blind, Placebo-Controlled Dose Escalation Study of NFC-1 in Adolescents With Attention-Deficit Hyperactivity Disorder (NFC1-GREAT)", Clinical Trials.gov Identifier: NCT02286817, Nov. 10, 2014.
Van Ameringen, Michael; et al., "Anticonvulsants in Anxiety Disorders", CPA Bulletin de l'APC (Aug. 2003).
Wittmann, Marion et al., "Activation of Group III mGluRs Inhibits GABAergic and Glutamatergic Transmissiokn in the Substantia Nigra Pars Reticulata", Journal of Neurophysiology, 1960-1968 (2001).
International Search Report and Written Opinion issued in PCT/US2016/050573, dated Dec. 21, 2016.
International Search Report and Written Opinion issued in PCT/US2016/050580, dated Dec. 20, 2016.
International Search Report and Written Opinion issued in PCT/US2016/050581, dated Dec. 21, 2016.
Office Action, dated May 7, 2018, issued in corresponding Canadian Patent Application No. 2,807,505.
Rule 132 Declaration filed in U.S. Appl. No. 15/258,977, filed Sep. 7, 2016.
Muhle et al., The genetics of autism, Pediatrics, 2004, 113:e472-86.
Pinto et al., Functional impact of global rare copy number variation in autism spectrum disorders, Nature, 2010, 466: 368-375.
Glessner et al., Autism genome-wide copy number variation reveals ubiquitin and neuronal genes. Nature, 2009, 459: 569-573.
Buxbaum et al., Association between a GABRB3 polymorphism and autism, Mol Psychiatry, 2002, 7:311-316.
Matsunami et al., Identification of Rare Recurrent Copy Number Variants in High-Risk Autism Families and Their Prevalence in a Large ASD Population, PLoS One, 2013, e52239.
Moreno-De-Luca et al., Using large clinical data sets to infer pathogenicity for rare copy number variants in autism cohorts, Mol Psychiatry, 2013, 18:1090-1095.
Serajee et al., The metabotropic glutamate receptor 8 gene at 7q31: partial duplication and possible association with autism, J Med Genet, 2003, 40:e42.
Cusco et al., Autism-specific copy number variants further implicate the phosphatidylinositol signaling pathway and the glutamatergic synapse in the etiology of the disorder, Hum Mol Genet, 2009, 18:1795-1804.
Wang et al., PennCNV: an integrated hidden Markov model designed for high-resolution copy number variation detection in whole-genome SNP genotyping data, Genome Res, 2007, 17:1665-1674.
Gai et al., , Rare structural variation of synapse and neurotransmission genes in autism. Mol. Psychiatry, 2011, 17:402-411.
Mehta et al., mGluR5-antagonist mediated reversal of elevated stereotyped, repetitive behaviors in the VPA model of autism, Plos One 6, 2011, 25:e26077.
Delahanty et al., Maternal transmission of a rare GABRB3 signal peptide variant is associated with autism, Mol Psychiatry. Jan. 2011, 16:86-96.
Ghelardini et al., DM235 (sunifiram): a novel nootropic with potential as a cognitive enhancer, Naunyn-Schmiedeberg's Archives of Pharmacology, 2002, 365:419-26.
Klopocki et al., Copy-number variations, noncoding sequences, and human phenotypes, Annu Rev Genet, 2011, 12:53-72.
GeneLoc Search Results for PRAME from http://genecards.weizmann.ac.il, 1 printed page, Sep. 23, 2015.
SNP linked to gene (geneID:23532) via contig annotation, from http://www.ncbi.nlm.nih.gov, pp. 1-16, printed on Sep. 23, 2015.
Hans et al. Neuroscience 2013—presentation abstract (Nov. 10, 2013), printed pp. 1-3.
STRING network view of PRAME from http://string.db.org, pp. 1-2, printed on Sep. 23, 2015.
International Search Report issued in PCT/US2012/045959, dated Sep. 7, 2012.
International Search Report issued in PCT/US2015/042354, dated Nov. 3, 2015.
International Search Report issued in PCT/US2016/037596, dated Sep. 16, 2016.

* cited by examiner

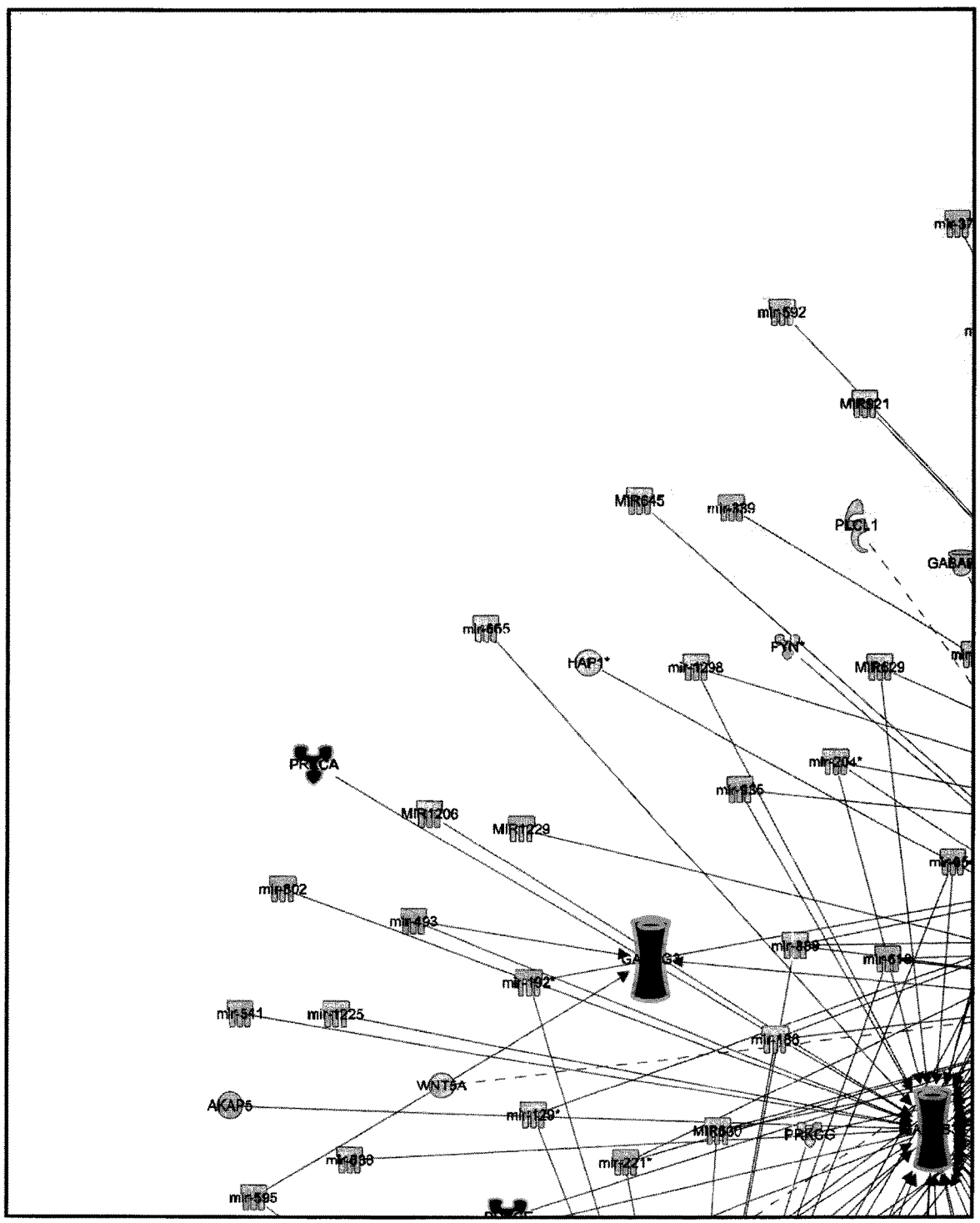
FIG. 3A (Top left)

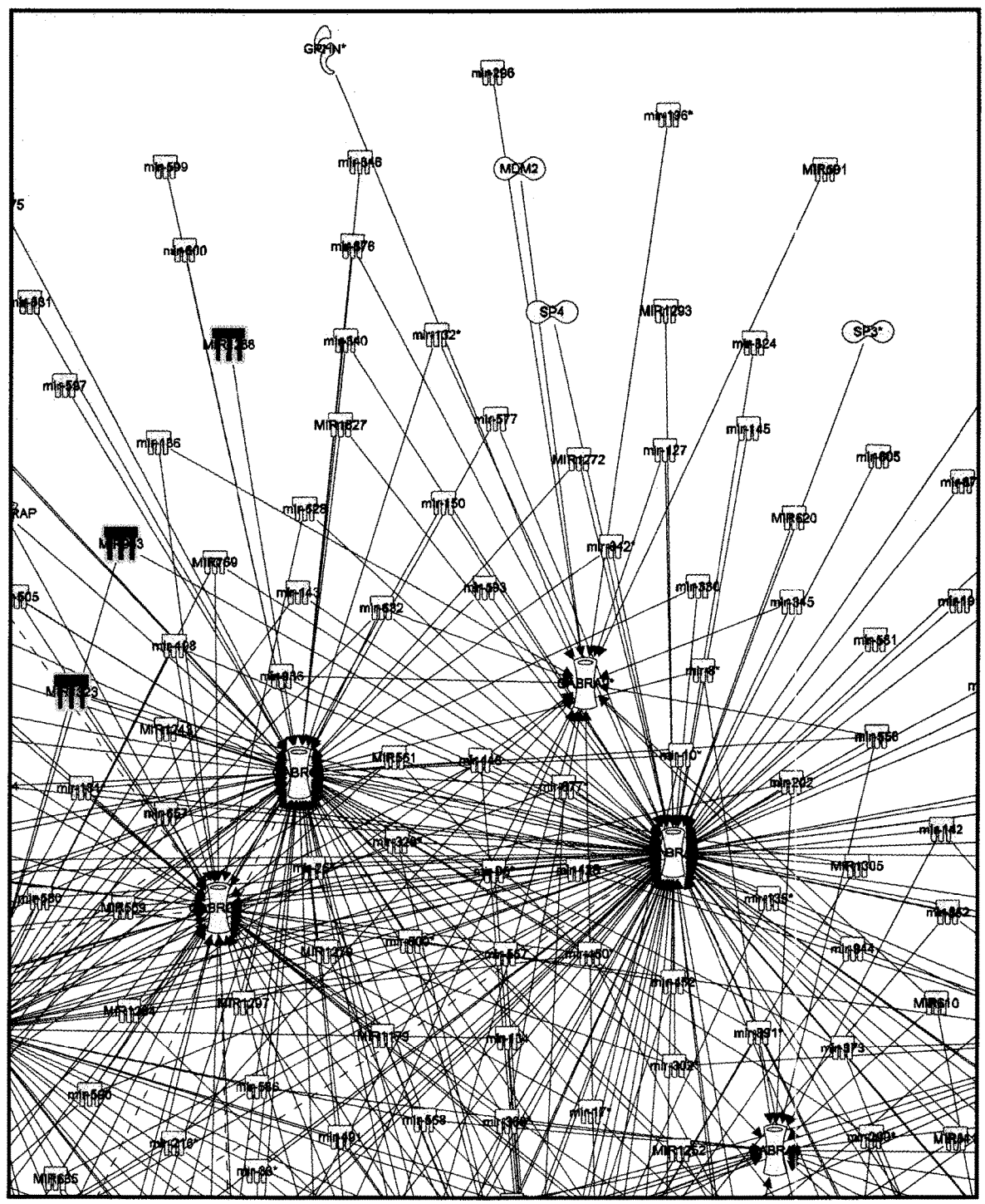
FIG. 3B (Top center)

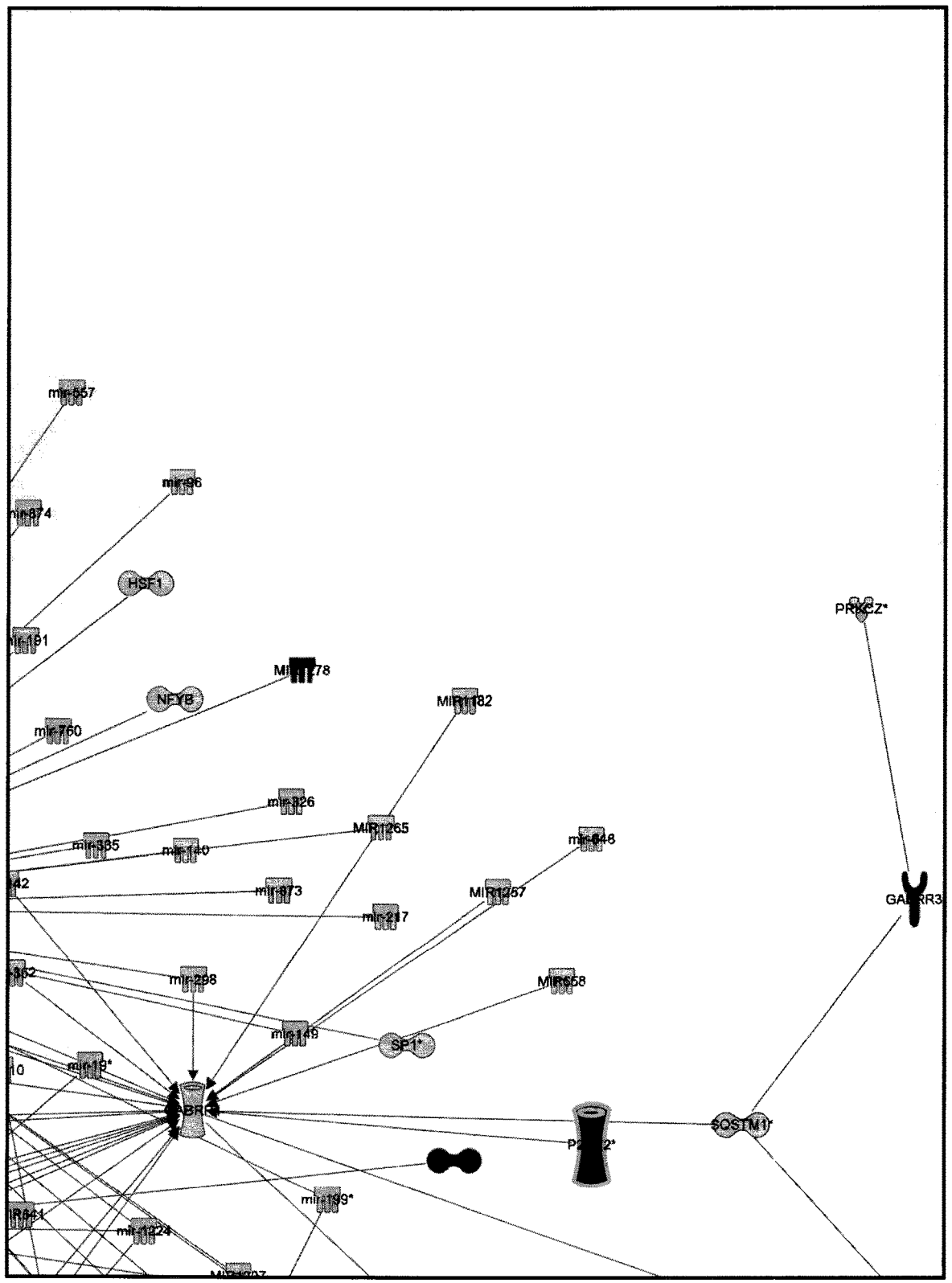
FIG. 3C (Top right)

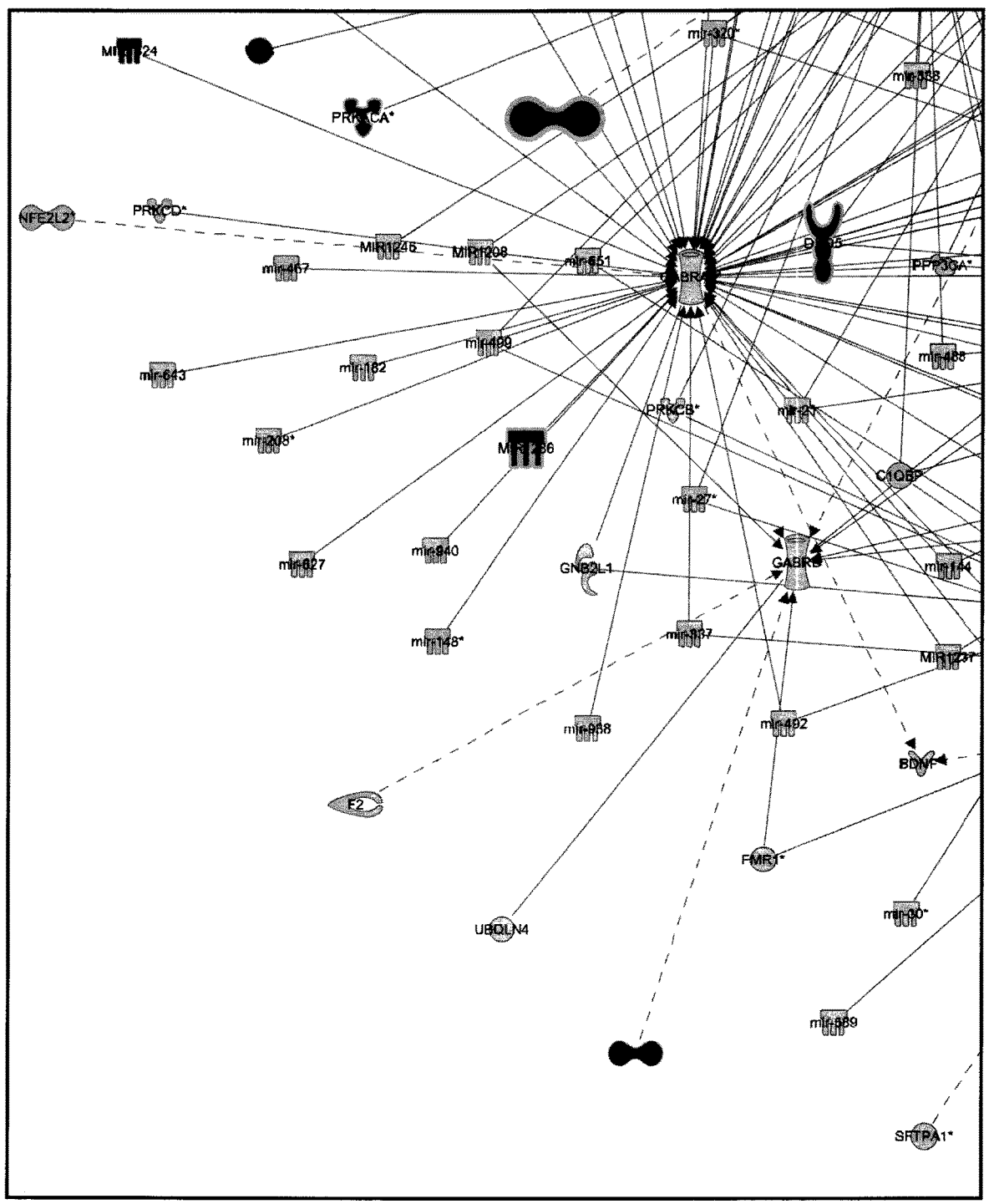
FIG. 3D (Bottom left)

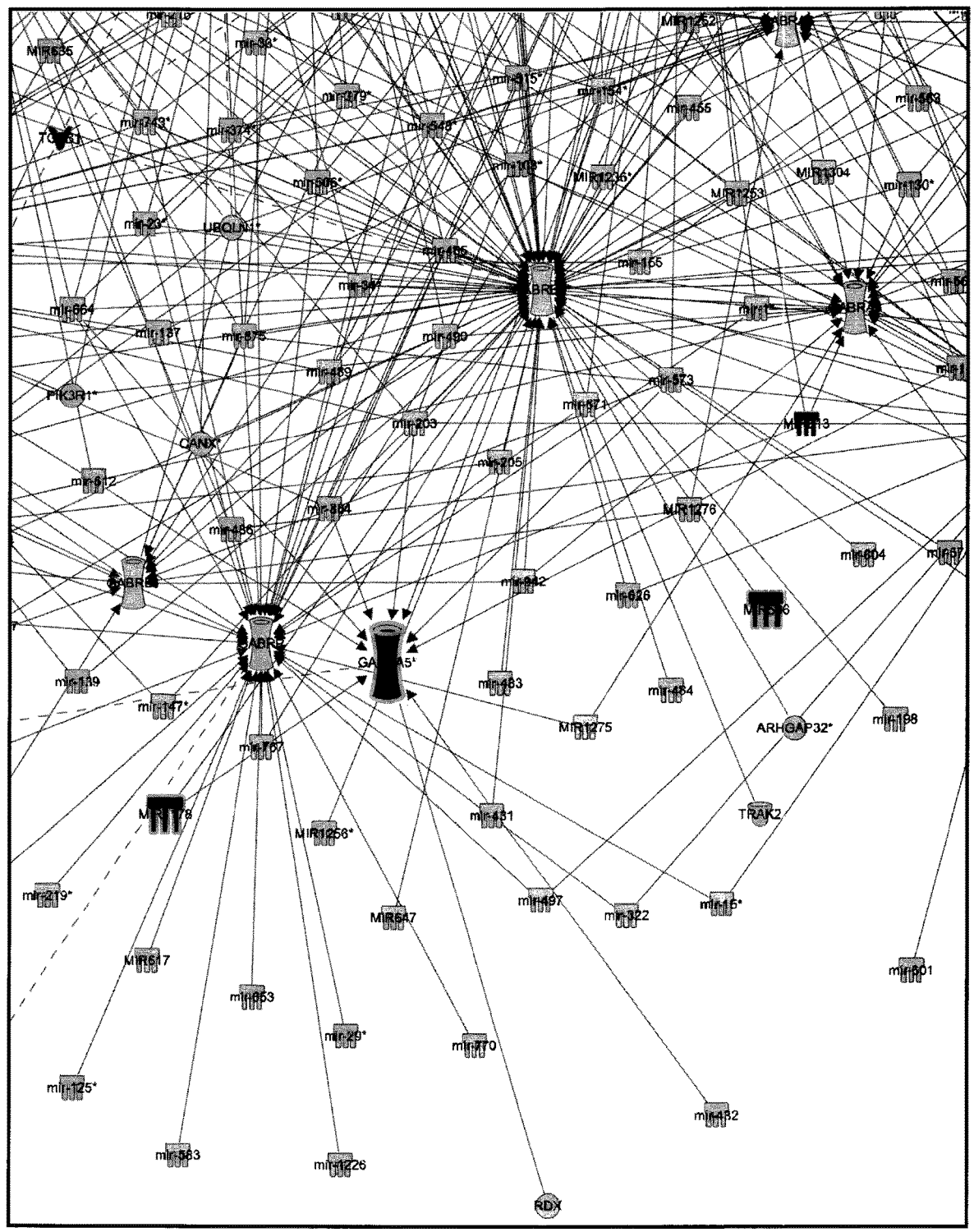
FIG. 3E (Bottom center)

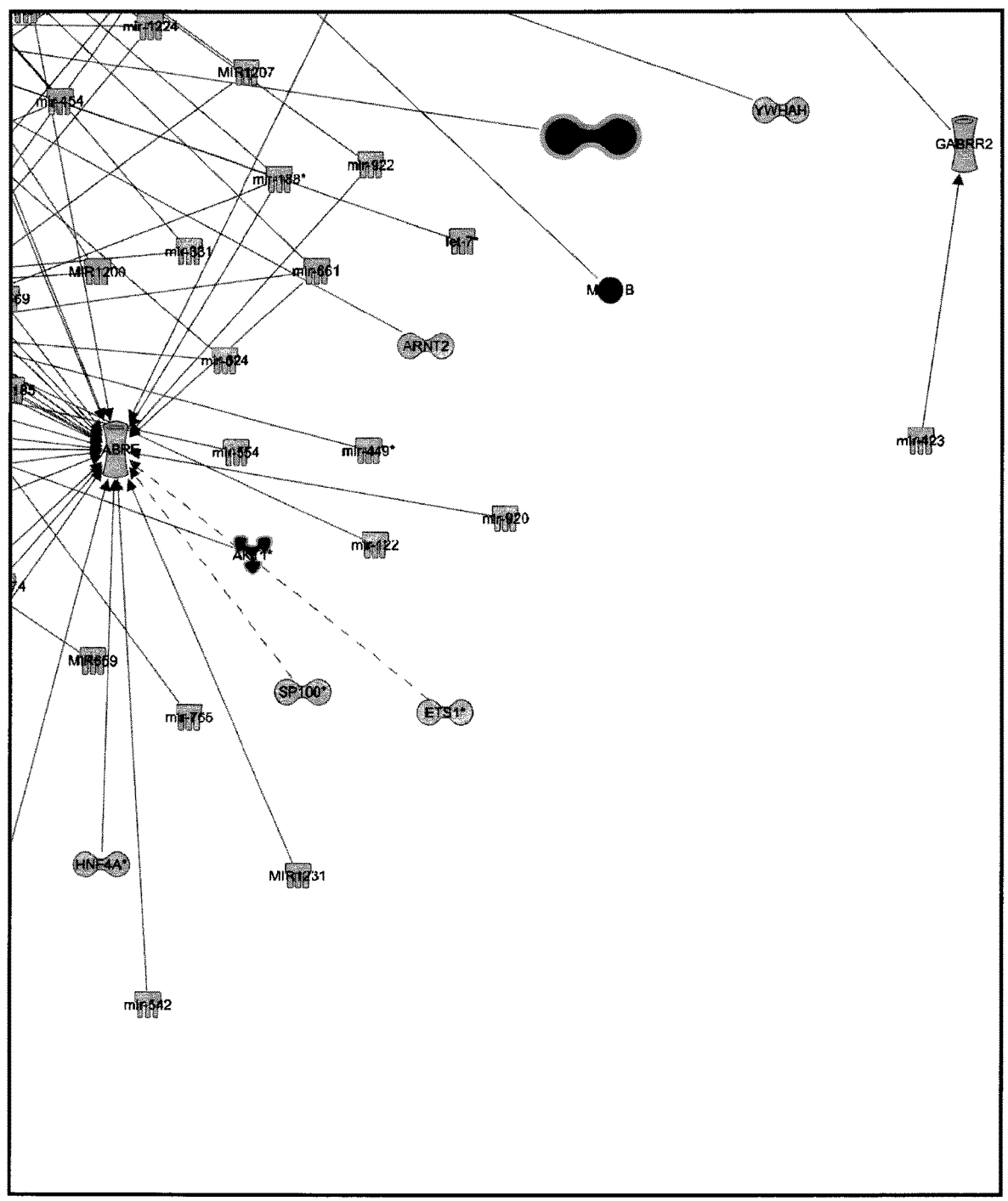
FIG. 3F (Bottom right)

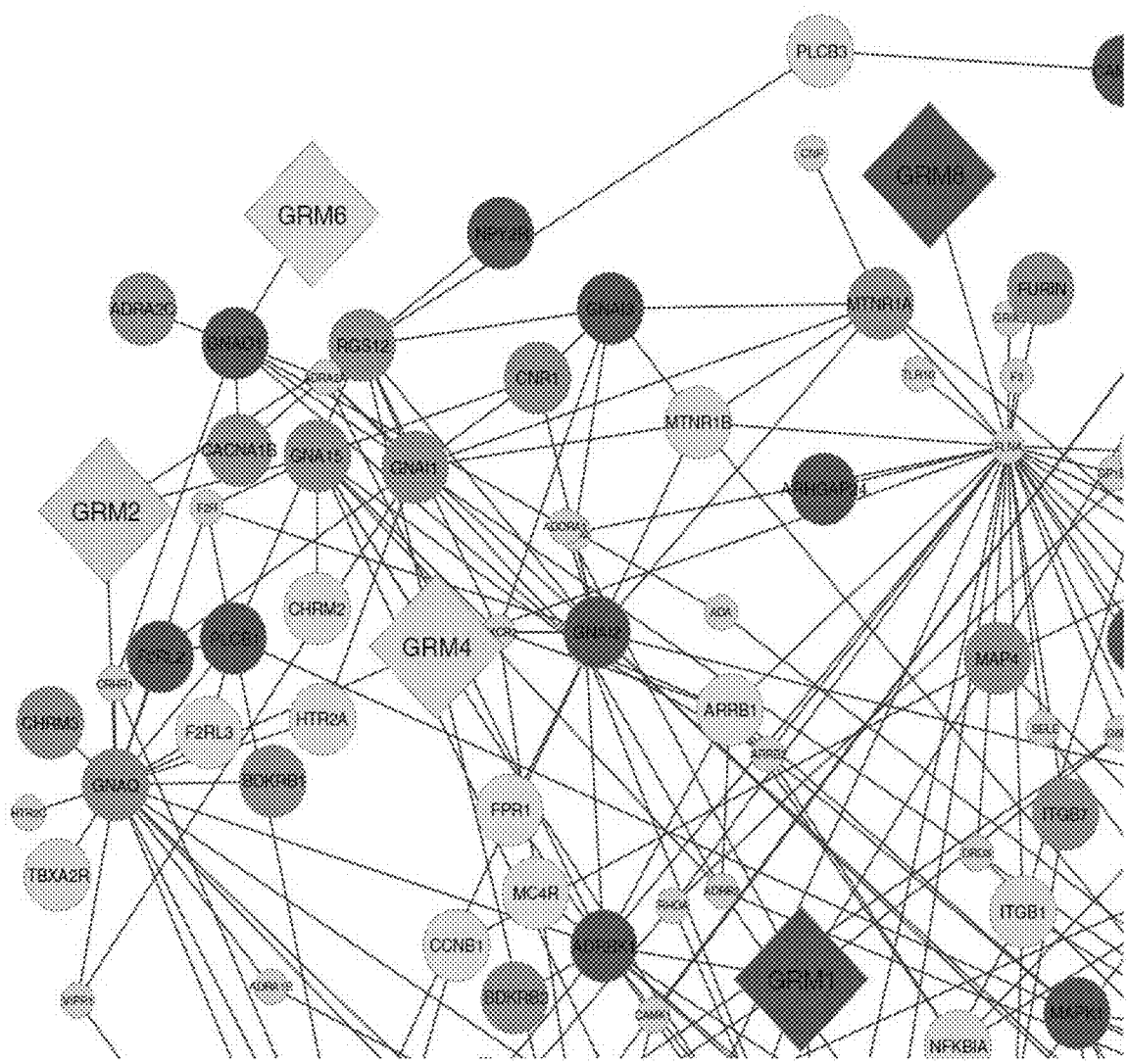
FIG. 6A (top left)

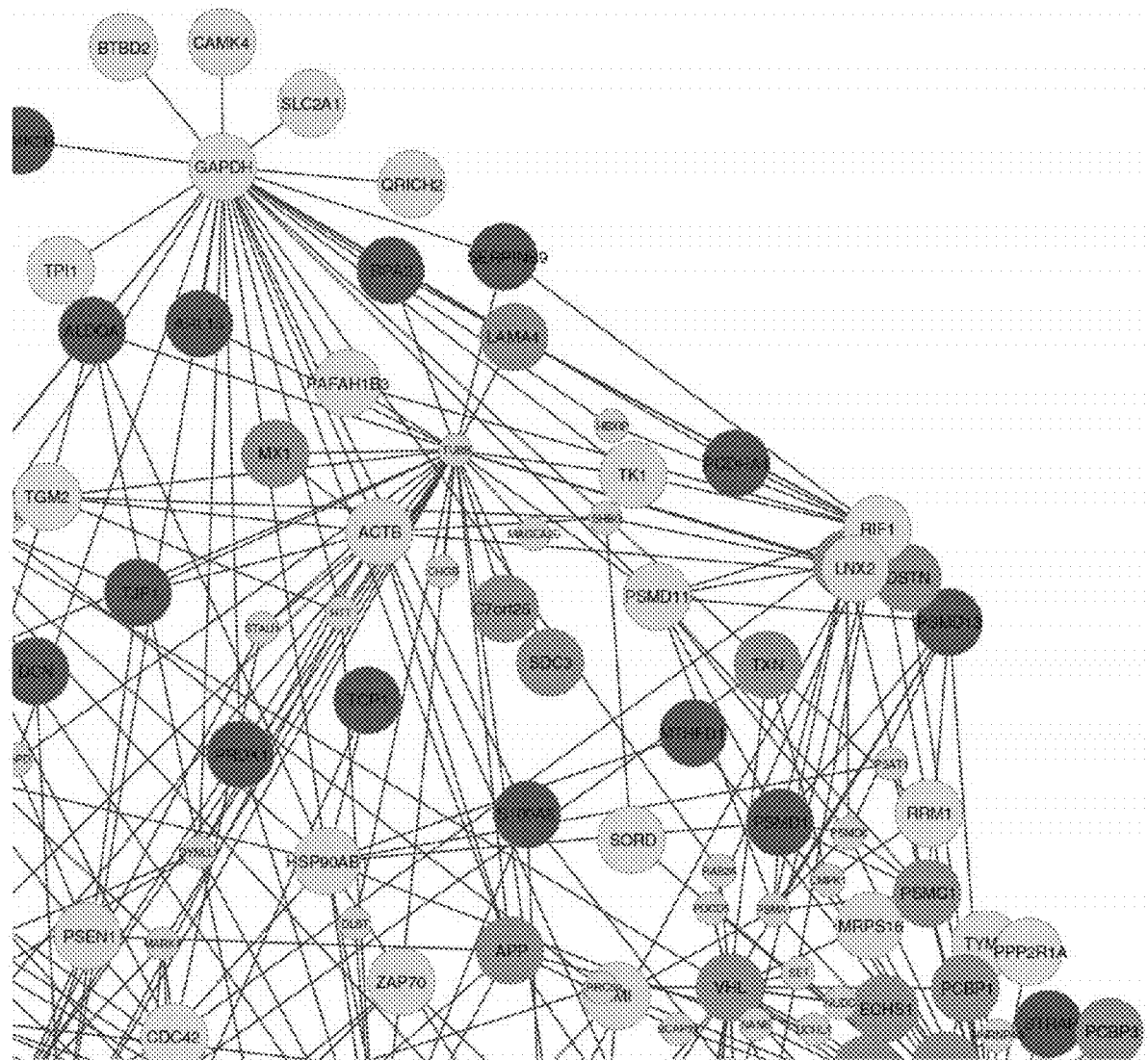
FIG. 6B (top right)

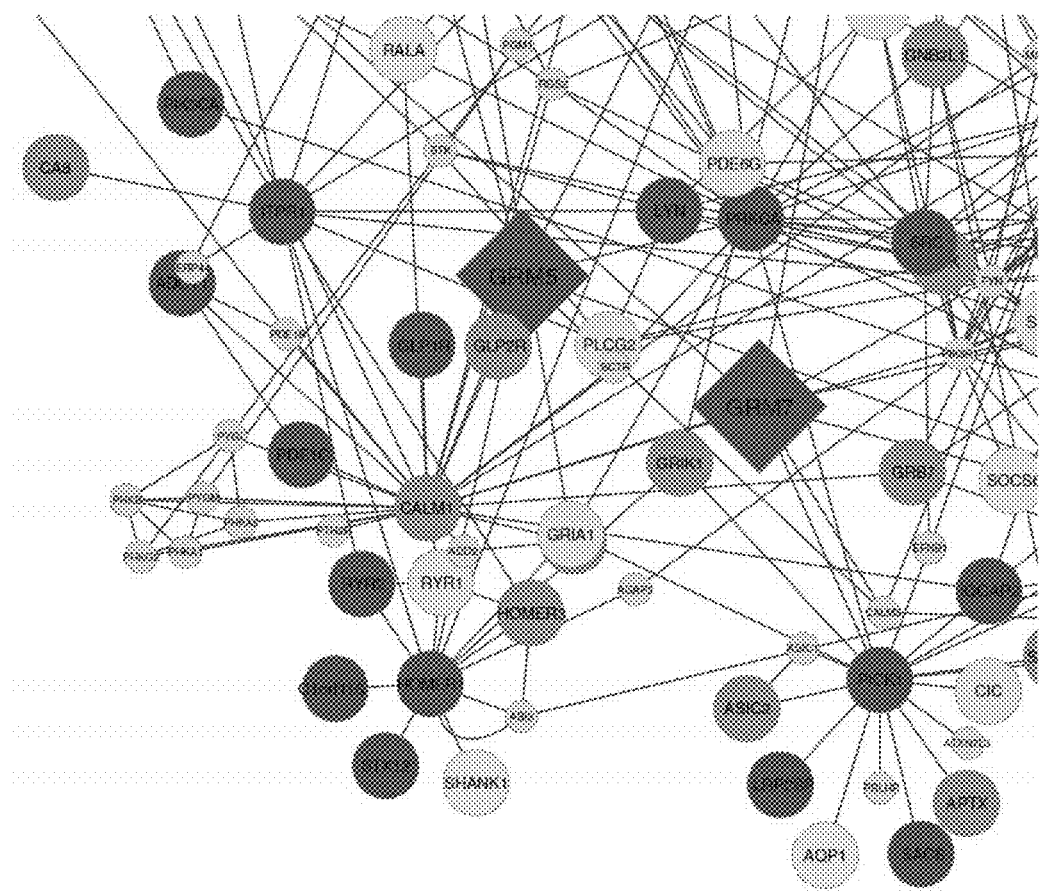
FIG. 6C (bottom left)

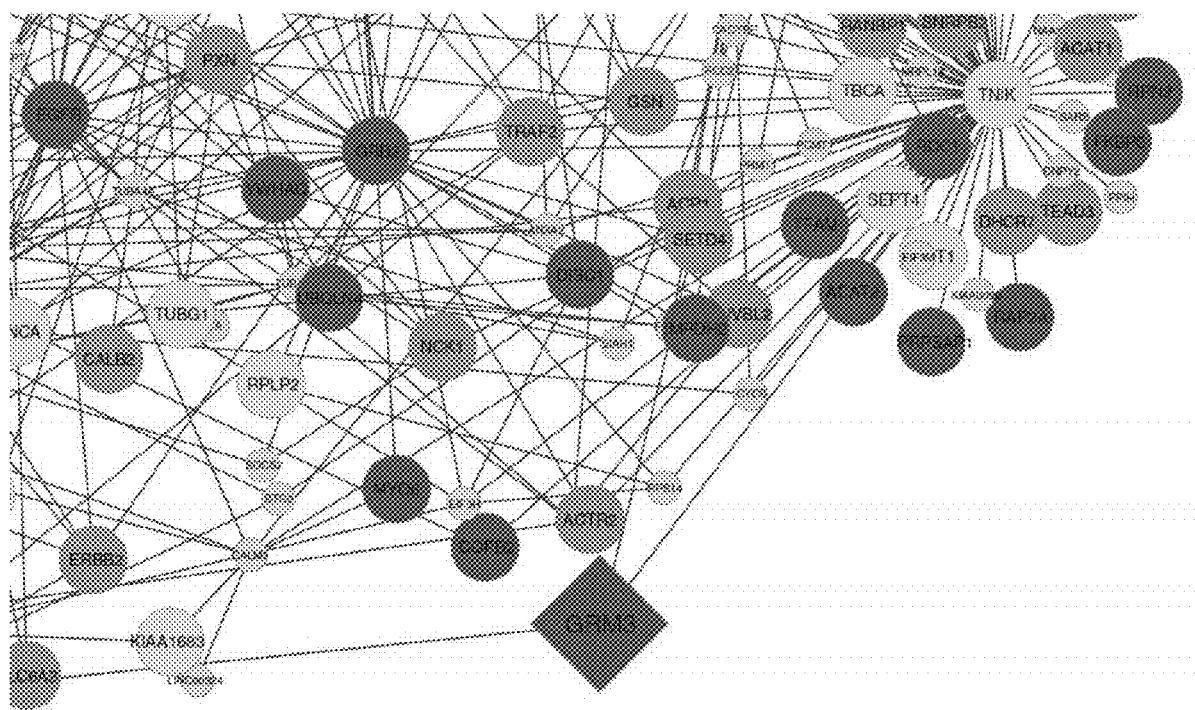
FIG. 6D (bottom right)

| CNV | gene | bands | locus | Size (Kb) | # SNP | # Case | # Ctrl | P | OR |
|---|---|---|---|---|---|---|---|---|---|
| | | | Most significant CNVRs within genes across the mGluR GFIN | | | | | | |
| dup | CACNA1B | 9q34.3 | chr9:140767745-140774721 | 6.98 | 2 | 11 | 0 | 4.21E-04 | inf |
| dup | CNR1 | 6q15 | chr6:88858724-88861698 | 2.98 | 1 | 15 | 8 | 9.39E-02 | 1.93 |
| dup | ECHS1 | 10q26.3 | chr10:135174203-135183094 | 8.89 | 2 | 10 | 0 | 8.54E-04 | inf |
| dup | HOMER3 | 19p13.11 | chr19:19050957-19054720 | 3.76 | 2 | 9 | 3 | 6.68E-02 | 3.08 |
| del | PSMD1 | 2q37.1 | chr2:232025285-232035793 | 10.51 | 1 | 14 | 2 | 1.77E-03 | 7.20 |
| dup | RANBP1 | 22q11.21 | chr22:20107729-20117344 | 9.62 | 1 | 13 | 3 | 9.24E-03 | 4.46 |
| del | RYR2 | 1q43 | chr1:237273380-237275393 | 2.01 | 1 | 4 | 0 | 5.93E-02 | inf |
| del | TJP1 | 15q13.1 | chr15:29812778-30178613 | 365.84 | 62 | 4 | 0 | 5.93E-02 | inf |
| dup | TRAF2 | 9q34.3 | chr9:139776401-139821067 | 44.67 | 3 | 6 | 1 | 5.83E-02 | 6.16 |
| dup | TUBA3C | 13q12.11 | chr13:19743860-19748709 | 4.85 | 4 | 17 | 8 | 4.70E-02 | 2.18 |
| | | | Most significant CNVRs within GRM hubs of mGluR GFIN | | | | | | |
| del | GRM1 | 6q24.3 | chr6:146615383-146633818 | 18.44 | 3 | 2 | 0 | 2.44E-01 | inf |
| del | GRM3 | 7q21.12 | chr7:86410689-86455535 | 44.85 | 9 | 1 | 0 | 4.94E-01 | inf |
| del | GRM4 | 6p21.31 | chr6:33986091-34072561 | 86.47 | 26 | 0 | 1 | 1.00E+00 | -inf |
| del | GRM5 | 11q14.3 | chr11:88768276-88841459 | 73.18 | 7 | 4 | 0 | 5.96E-02 | inf |
| dup | GRM6 | 5q35.3 | chr5:178313079-178547566 | 234.49 | 51 | 0 | 2 | 5.00E-01 | -inf |
| del | GRM7 | 3p26.1 | chr3:7169454-7197715 | 28.26 | 11 | 2 | 0 | 2.44E-01 | inf |
| del | GRM8 | 7q31.33 | chr7:126405246-126457778 | 52.53 | 11 | 1 | 0 | 4.94E-01 | inf |

Figure 9

| CNV | gene(s) | bands | locus | Size (Kb) | # SNP | # Case | # Ctrl | P | OR |
|---|---|---|---|---|---|---|---|---|---|
| dup | SKI | 1p36.33 | chr1:2204755-2211849 | 7.10 | 3 | 6 | 1 | 5.87E-02 | 6.15 |
| del | SMARCC1 | 3p21.31 | chr3:47749708-47749708 | 0.00 | 1 | 10 | 2 | 1.74E-02 | 5.13 |
| del | HDAC2 | 6q21 | chr6:114260720-114273646 | 12.93 | 5 | 4 | 0 | 5.96E-02 | inf |
| del | HDAC9 | 7p21.1 | chr7:18375246-18384157 | 8.91 | 2 | 4 | 0 | 5.96E-02 | inf |
| dup | PLEC PARP10 | 8q24.3 | chr8:145046663-145059425 | 12.76 | 1 | 243 | 125 | 4.06E-11 | 2.04 |
| del | HDAC7 | 12q13.11 | chr12:48178513-48178604 | 0.09 | 2 | 7 | 1 | 3.26E-02 | 7.17 |
| dup | SNORD115-43 SNORD115-42 UBE3A SNORD115-47 SNORD115-45 SNORD115-44 SNORD115-48 SNORD115-36 SNORD109A SNORD115-29 SNORD109B SNORD115-10 SNORD115-11 | 15q11.2 | chr15:25491630-25606727 | 115.10 | 11 | 19 | 0 | 1.50E-06 | inf |
| del | PML STOML1 | 15q24.1 | chr15:74247944-74343330 | 95.39 | 20 | 6 | 0 | 1.45E-02 | inf |
| del | PTPN9 SIN3A | 15q24.2 | chr15:75718670-75806911 | 88.24 | 4 | 7 | 0 | 7.19E-03 | inf |
| Most significant CNVRs within MXD hubs of MXD GFIN | | | | | | | | | |
| del | SNRNP27 MXD1 | 2p13.3 | chr2:70112581-70173629 | 61.05 | 10 | 1 | 0 | 4.94E-01 | inf |
| dup | ZFYVE28 MXD4 | 4p16.3 | chr4:2256717-2287420 | 30.70 | 4 | 2 | 0 | 2.44E-01 | inf |
| | GPRIN1 RAB24 MIR4281 HK3 UNC5A TSPAN17 SNCB ZNF346 LMAN2 EIF4E1B NSD1 PRELID1 FGFR4 MXD3 | 5q35.2 | | | | | | | |
| del | UIMC1 | 5q35.3 | chr5:176024881-176780544 | 755.66 | 95 | 1 | 0 | 4.94E-01 | inf |

Figure 10

| CNV | gene | bands | locus | Size (Kb) | # SNP | # Case | # Ctrl | P | OR |
|---|---|---|---|---|---|---|---|---|---|
| del | ADCY1 | 7p12.3 | chr7:45598469-45620959 | 22491 | 2 | 1 | 0 | 4.94E-01 | inf |
| dup | ADD1 | 4p16.3 | chr4:2906285-3080173 | 173889 | 28 | 3 | 0 | 1.21E-01 | inf |
| del | C4orf3 | 4q26 | chr4:120111190-120399505 | 288316 | 31 | 1 | 0 | 4.94E-01 | inf |
| dup | CALM1 | 14q32.11 | chr14:90843792-90868442 | 24651 | 4 | 2 | 0 | 2.44E-01 | inf |
| del | GLP1R | 6p21.2 | chr6:39022698-39055516 | 32819 | 23 | 1 | 0 | 4.94E-01 | inf |
| dup | GLP2R | 17p13.1 | chr17:9708956-9826778 | 117823 | 45 | 1 | 0 | 4.94E-01 | inf |
| dup | GRB7 | 17q12 | chr17:37834542-37922259 | 87718 | 2 | 1 | 0 | 4.94E-01 | inf |
| del | IQGAP2 | 5q13.3 | chr5:75795407-75805105 | 9699 | 4 | 1 | 0 | 4.94E-01 | inf |
| del | PDE1C | 7p14.3 | chr7:32225283-32228302 | 3020 | 5 | 3 | 0 | 1.21E-01 | inf |
| del | PTH2R | 2q34 | chr2:209280931-209297026 | 16096 | 4 | 0 | 1 | 1.00E+00 | 0 |

Figure 11

| CNVR | Genes | Bands | Size (Kb) | No. of SNP | No. of Case | No. of Control | All | | Europe | | Africa | |
|---|---|---|---|---|---|---|---|---|---|---|---|---|
| | | | | | | | P-value | OR | P-value | OR | P-value | OR |
| del | ZNF280B | 22q11.22 | 53.4 | 13 | 130 | 0 | 2.56E-57 | Inf | 1.94E-33 | Inf | 3.34E-04 | Inf |
| del | PARP8 | 5q11.1 | 47.7 | 8 | 70 | 8 | 2.76E-22 | 15.1 | 3.84E-13 | 12.0 | 2.69E-06 | 40.9 |
| dup | GABRB3 | 15q12 | 49.0 | 20 | 28 | 0 | 7.60E-13 | Inf | 1.50E-06 | Inf | 3.34E-04 | Inf |
| dup | GABRG3 | 15q12 | 135.3 | 13 | 27 | 1 | 3.72E-11 | Inf | 1.60E-05 | 19.5 | 3.34E-04 | Inf |
| dup | HERC2 | 15q13.1 | 84.4 | 2 | 24 | 0 | 4.12E-11 | Inf | 6.17E-06 | Inf | 3.34E-04 | Inf |

Figure 12

| Gene family | | Enriched genes | | Cases | | Controls | | Gene Network Association | | | |
|---|---|---|---|---|---|---|---|---|---|---|---|
| Name | Size | No. | Frequency | No. | Frequency | No. | Frequency | P fisher | Enrichment | P perm | |
| BRF | 2 | 242/326 | 0.742 | 567 | 0.123 | 370 | 0.078 | 3.30E-13 | 1.65 | 0.040 | |
| CCL | 24 | 108/144 | 0.75 | 231 | 0.05 | 129 | 0.027 | 5.62E-09 | 1.88 | 0.008 | |
| CCNT | 2 | 183/254 | 0.72 | 613 | 0.133 | 381 | 0.081 | 1.10E-16 | 1.75 | 0.007 | |
| ELAVL | 4 | 108/156 | 0.692 | 327 | 0.071 | 152 | 0.032 | 6.87E-18 | 2.3 | 0.043 | |
| ERCC | 7 | 263/369 | 0.713 | 836 | 0.182 | 560 | 0.119 | 7.67E-18 | 1.65 | 0.035 | |
| GRM | 8 | 124/181 | 0.685 | 265 | 0.058 | 153 | 0.032 | 2.40E-09 | 1.82 | 0.043 | |
| GTF2H | 5 | 152/223 | 0.682 | 391 | 0.085 | 233 | 0.049 | 3.21E-12 | 1.79 | 0.049 | |
| KIAA | 106 | 268/373 | 0.718 | 988 | 0.215 | 647 | 0.137 | 3.12E-23 | 1.72 | 0.045 | |
| KPNA | 7 | 256/367 | 0.698 | 560 | 0.122 | 369 | 0.078 | 1.26E-12 | 1.63 | 0.028 | |
| MXD | 3 | 52/64 | 0.813 | 366 | 0.08 | 156 | 0.033 | 3.83E-23 | 2.53 | 0.042 | |

Figure 13

| | | | | | | | | |
|---|---|---|---|---|---|---|---|---|
| POU5F | 2 | 94/130 | 0.723 | 293 | 0.064 | 131 | 0.028 | 2.96E−17 | 2.38 | 0.041 |
| RAD | 7 | 218/309 | 0.706 | 535 | 0.116 | 339 | 0.072 | 9.68E−14 | 1.7 | 0.042 |
| SAP | 4 | 111/150 | 0.74 | 274 | 0.06 | 151 | 0.032 | 9.61E−11 | 1.92 | 0.040 |
| SMAD | 8 | 845/1,225 | 0.69 | 1,782 | 0.387 | 1,424 | 0.302 | 1.81E−18 | 1.46 | 0.039 |
| SMARCC | 2 | 106/147 | 0.721 | 239 | 0.052 | 131 | 0.028 | 1.22E−09 | 1.92 | 0.043 |
| SMC | 5 | 88/120 | 0.733 | 336 | 0.073 | 176 | 0.037 | 1.71E−14 | 2.03 | 0.034 |

Figure 13 Continued

| Gene Family Member | Enriched Genes | | Cases | | Controls | | Gene Network Association | | |
|---|---|---|---|---|---|---|---|---|---|
| | No. | Frequency | No. | Frequency | # | Frequency | $P_{fisher}$ | Enrichment | $P_{perm}$ |
| AKAP13 | 7/7 | 1.00 | 16 | 0.0035 | 1 | 0.0002 | 1.14E-04 | 16.43 | 0.012 |
| BAG1 | 7/7 | 1.00 | 15 | 0.0032 | 1 | 0.0002 | 2.18E-04 | 15.40 | 0.014 |
| CALM1 | 9/10 | 0.90 | 14 | 0.0030 | 1 | 0.0002 | 4.16E-04 | 14.37 | 0.002 |
| CASP6 | 16/17 | 0.94 | 46 | 0.0100 | 6 | 0.0013 | 2.96E-09 | 7.91 | 0.012 |
| GTF2H3 | 23/26 | 0.88 | 42 | 0.0091 | 8 | 0.0017 | 3.66E-07 | 5.41 | 0.009 |
| MAP3K5 | 11/12 | 0.92 | 34 | 0.0074 | 4 | 0.0008 | 2.02E-07 | 8.76 | 0.012 |
| NCOR1 | 9/10 | 0.90 | 26 | 0.0056 | 2 | 0.0004 | 1.11E-06 | 13.37 | 0.004 |
| PARP1 | 5/5 | 1.00 | 5 | 0.0011 | 0 | 0.0000 | 2.95E-02 | inf | 0.012 |
| PTPN13 | 6/6 | 1.00 | 9 | 0.0019 | 0 | 0.0000 | 1.75E-03 | inf | 0.007 |
| TCEA1 | 22/26 | 0.85 | 39 | 0.0084 | 7 | 0.0015 | 5.94E-07 | 5.74 | 0.009 |

FIGURE 14

| | A | B | C | D | E | F | G | H | I | J | K |
|---|---|---|---|---|---|---|---|---|---|---|---|
| 1 | sym | locus | numCases | totalCases | numControls | totalControls | fCase | fControl | pVal | oddsRatio | enrichment |
| 2 | ACAT1 | dup:chr11:107957478-108034124 | 4 | 4602 | 1 | 4722 | 0.00086919 | 0.00021177 | 0.17949275 | 4.10700304 | case |
| 3 | ACAT2 | del:chr6:160152776-160207570 | 1 | 4602 | 0 | 4722 | 0.0002173 | 0 | 0.49356499 | None | case |
| 4 | ACP1 | dup:chr2:238975-272926 | 2 | 4602 | 0 | 4722 | 0.00043459 | 0 | 0.24357959 | None | case |
| 6 | ACTR2 | dup:chr2:65425014-65495283 | 1 | 4602 | 0 | 4722 | 0.0002173 | 0 | 0.49356499 | None | case |
| 7 | ADCY1 | del:chr7:45598469-45620959 | 1 | 4602 | 0 | 4722 | 0.0002173 | 0 | 0.49356499 | None | case |
| 8 | ADD1 | dup:chr4:2906285-3080173 | 3 | 4602 | 0 | 4722 | 0.00065189 | 0 | 0.12019589 | None | case |
| 9 | ADRA2C | dup:chr4:3505449-3780071 | 3 | 4602 | 0 | 4722 | 0.00065189 | 0 | 0.12019589 | None | case |
| 10 | ADRBK1 | del:chr11:67033077-67164494 | 2 | 4602 | 0 | 4722 | 0.00043459 | 0 | 0.24357959 | None | case |
| 11 | AGAP2 | dup:chr12:58112190-58177292 | 2 | 4602 | 0 | 4722 | 0.00043459 | 0 | 0.24357959 | None | case |
| 12 | ALDOA | del:chr16:30046043-30141257 | 8 | 4602 | 3 | 4722 | 0.00173837 | 0.00063532 | 0.10506275 | 2.73922508 | case |
| 13 | APTX | dup:chr9:32954680-33083731 | 1 | 4602 | 0 | 4722 | 0.0002173 | 0 | 0.49356499 | None | case |
| 15 | ARHGAP24 | del:chr4:86517054-86532911 | 1 | 4602 | 0 | 4722 | 0.0002173 | 0 | 0.49356499 | None | case |
| 16 | ARL15 | del:chr5:53368171-53399217 | 1 | 4602 | 0 | 4722 | 0.0002173 | 0 | 0.49356499 | None | case |
| 18 | BDKRB1 | dup:chr14:96054262-96728753 | 1 | 4602 | 0 | 4722 | 0.0002173 | 0 | 0.49356499 | None | case |
| 19 | BDKRB2 | dup:chr14:96054262-96728753 | 1 | 4602 | 0 | 4722 | 0.0002173 | 0 | 0.49356499 | None | case |
| 21 | C1orf116 | del:chr1:207203757-207236524 | 1 | 4602 | 0 | 4722 | 0.0002173 | 0 | 0.49356499 | None | case |
| 22 | C4orf3 | del:chr4:120111190-120399505 | 1 | 4602 | 0 | 4722 | 0.0002173 | 0 | 0.49356499 | None | case |
| 23 | C7orf25 | dup:chr7:42869485-43178373 | 1 | 4602 | 0 | 4722 | 0.0002173 | 0 | 0.49356499 | None | case |
| 24 | CA8 | dup:chr8:60997356-61231164 | 1 | 4602 | 0 | 4722 | 0.0002173 | 0 | 0.49356499 | None | case |
| 25 | CACNA1B | dup:chr9:140767745-140774721 | 11 | 4602 | 0 | 4722 | 0.00239027 | 0 | 0.00042088 | None | case |
| 26 | CALB2 | dup:chr16:70786633-71429923 | 2 | 4602 | 0 | 4722 | 0.00043459 | 0 | 0.24357959 | None | case |
| 27 | CALM1 | dup:chr14:90843792-90868442 | 2 | 4602 | 0 | 4722 | 0.00043459 | 0 | 0.24357959 | None | case |
| 28 | CAMK2B | del:chr7:44255034-44334542 | 1 | 4602 | 0 | 4722 | 0.0002173 | 0 | 0.49356499 | None | case |
| 32 | CHP | del:chr15:41486991-41529712 | 6 | 4602 | 3 | 4722 | 0.00130378 | 0.00063532 | 0.24129356 | 2.0535248 | case |
| 34 | CHRM3 | dup:chr1:239821058-239827726 | 2 | 4602 | 0 | 4722 | 0.00043459 | 0 | 0.24357959 | None | case |
| 36 | CNPY2 | dup:chr12:56325420-56946239 | 1 | 4602 | 0 | 4722 | 0.0002173 | 0 | 0.49356499 | None | case |
| 37 | CNR1 | dup:chr6:88858724-88861698 | 15 | 4602 | 8 | 4722 | 0.00325945 | 0.0016942 | 0.09389401 | 1.92691302 | case |
| 38 | COPB2 | del:chr3:139101777-139110135 | 1 | 4602 | 1 | 4722 | 0.0002173 | 0.00021177 | 0.7435504 | 1.02608129 | case |
| 39 | DCN | del:chr12:91476569-91662308 | 2 | 4602 | 0 | 4722 | 0.00043459 | 0 | 0.24357959 | None | case |
| 40 | DHCR7 | dup:chr11:70876436-71281859 | 1 | 4602 | 0 | 4722 | 0.0002173 | 0 | 0.49356499 | None | case |
| 41 | DISC1 | del:chr1:231843962-231886652 | 1 | 4602 | 0 | 4722 | 0.0002173 | 0 | 0.49356499 | None | case |
| 42 | DSTN | dup:chr20:17490410-17691406 | 1 | 4602 | 0 | 4722 | 0.0002173 | 0 | 0.49356499 | None | case |
| 43 | ECHS1 | dup:chr10:135174203-135183094 | 10 | 4602 | 0 | 4722 | 0.00217297 | 0 | 0.00085367 | None | case |

FIGURE 15

| | A | B | C | D | E | F | G | H | I | J | K |
|---|---|---|---|---|---|---|---|---|---|---|---|
| 44 | EGFR | del:chr7:54727310-55442774 | 1 | 4602 | 0 | 4722 | 0.0002173 | 0 | 0.49356499 | None | case |
| 46 | ERBB2 | dup:chr17:37834542-37922259 | 1 | 4602 | 0 | 4722 | 0.0002173 | 0 | 0.49356499 | None | case |
| 47 | ERP44 | del:chr9:102723693-102744008 | 4 | 4602 | 2 | 4722 | 0.00086919 | 0.00042355 | 0.3317105 | 2.05306655 | case |
| 48 | F2RL2 | del:chr5:75875630-75913784 | 3 | 4602 | 2 | 4722 | 0.00065189 | 0.00042355 | 0.48793311 | 1.5394651 | case |
| 50 | FKBP3 | del:chr14:45578044-45619217 | 2 | 4602 | 0 | 4722 | 0.00043459 | 0 | 0.24357959 | None | case |
| 52 | FURIN | dup:chr15:91237231-91697710 | 1 | 4602 | 0 | 4722 | 0.0002173 | 0 | 0.49356499 | None | case |
| 54 | GLP1R | del:chr6:39022698-39055516 | 1 | 4602 | 0 | 4722 | 0.0002173 | 0 | 0.49356499 | None | case |
| 55 | GLP2R | dup:chr17:9708956-9826778 | 1 | 4602 | 0 | 4722 | 0.0002173 | 0 | 0.49356499 | None | case |
| 56 | GNA15 | dup:chr19:3133854-3136845 | 3 | 4602 | 0 | 4722 | 0.00065189 | 0 | 0.12019589 | None | case |
| 57 | GNAI1 | dup:chr7:79464196-79829843 | 1 | 4602 | 0 | 4722 | 0.0002173 | 0 | 0.49356499 | None | case |
| 58 | GNAI2 | del:chr3:50291785-50324671 | 2 | 4602 | 0 | 4722 | 0.00043459 | 0 | 0.24357959 | None | case |
| 59 | GNAI3 | del:chr1:110130405-110140977 | 1 | 4602 | 0 | 4722 | 0.0002173 | 0 | 0.49356499 | None | case |
| 60 | GNAO1 | del:chr16:56340096-56362724 | 3 | 4602 | 0 | 4722 | 0.00065189 | 0 | 0.12019589 | None | case |
| 61 | GNAQ | dup:chr9:80350999-80355515 | 1 | 4602 | 0 | 4722 | 0.0002173 | 0 | 0.49356499 | None | case |
| 62 | GNB2L1 | dup:chr5:180652242-180665489 | 1 | 4602 | 1 | 4722 | 0.0002173 | 0.00021177 | 0.7435504 | 1.02608129 | case |
| 64 | GRB2 | del:chr17:73358259-73374945 | 3 | 4602 | 0 | 4722 | 0.00065189 | 0 | 0.12019589 | None | case |
| 65 | GRB7 | dup:chr17:37834542-37922259 | 1 | 4602 | 0 | 4722 | 0.0002173 | 0 | 0.49356499 | None | case |
| 67 | GRIK1 | del:chr21:31213091-31226639 | 2 | 4602 | 0 | 4722 | 0.00043459 | 0 | 0.24357959 | None | case |
| 68 | GRM1 | del:chr6:146615383-146633818 | 2 | 4602 | 0 | 4722 | 0.00043459 | 0 | 0.24357959 | None | case |
| 69 | GRM3 | del:chr7:86410689-86455535 | 1 | 4602 | 0 | 4722 | 0.0002173 | 0 | 0.49356499 | None | case |
| 71 | GRM5 | del:chr11:88768276-88841459 | 4 | 4602 | 0 | 4722 | 0.00086919 | 0 | 0.05930489 | None | case |
| 73 | GRM7 | del:chr3:7169454-7197715 | 2 | 4602 | 0 | 4722 | 0.00043459 | 0 | 0.24357959 | None | case |
| 74 | GRM8 | del:chr7:126405246-126457778 | 1 | 4602 | 0 | 4722 | 0.0002173 | 0 | 0.49356499 | None | case |
| 75 | GSN | dup:chr9:123997647-124057682 | 1 | 4602 | 0 | 4722 | 0.0002173 | 0 | 0.49356499 | None | case |
| 76 | HNRNPA3 | del:chr2:178029851-178087851 | 1 | 4602 | 1 | 4722 | 0.0002173 | 0.00021177 | 0.7435504 | 1.02608129 | case |
| 77 | HOMER1 | del:chr5:78666514-78673236 | 2 | 4602 | 0 | 4722 | 0.00043459 | 0 | 0.24357959 | None | case |
| 78 | HOMER3 | dup:chr19:19050957-19054720 | 9 | 4602 | 3 | 4722 | 0.00195567 | 0.00063532 | 0.06684957 | 3.08229915 | case |
| 81 | HTT | dup:chr4:2906285-3080173 | 3 | 4602 | 0 | 4722 | 0.00065189 | 0 | 0.12019589 | None | case |
| 82 | IMPDH2 | del:chr3:49040462-49108428 | 1 | 4602 | 1 | 4722 | 0.0002173 | 0.00021177 | 0.7435504 | 1.02608129 | case |
| 83 | IQGAP2 | del:chr5:75795407-75805105 | 1 | 4602 | 0 | 4722 | 0.0002173 | 0 | 0.49356499 | None | case |
| 85 | ITGB7 | dup:chr12:53573903-53603737 | 3 | 4602 | 0 | 4722 | 0.00065189 | 0 | 0.12019589 | None | case |
| 86 | ITPR1 | del:chr3:4741821-4776094 | 1 | 4602 | 0 | 4722 | 0.0002173 | 0 | 0.49356499 | None | case |
| 88 | LAMA4 | dup:chr6:112573780-112614697 | 1 | 4602 | 0 | 4722 | 0.0002173 | 0 | 0.49356499 | None | case |
| 90 | LRP2BP | del:chr4:186143007-186336464 | 2 | 4602 | 1 | 4722 | 0.00043459 | 0.00021177 | 0.49034699 | 2.0526087 | case |

FIGURE 15 Continued

| | A | B | C | D | E | F | G | H | I | J | K |
|---|---|---|---|---|---|---|---|---|---|---|---|
| 91 | LYAR | dup:chr4:4082937-5142211 | 2 | 4602 | 0 | 4722 | 0.00043459 | 0 | 0.24357959 | None | case |
| 92 | LYN | del:chr8:56803179-56814308 | 1 | 4602 | 0 | 4722 | 0.0002173 | 0 | 0.49356499 | None | case |
| 93 | MAP4 | dup:chr3:47936671-48029118 | 1 | 4602 | 0 | 4722 | 0.0002173 | 0 | 0.49356499 | None | case |
| 94 | MAPK1 | del:chr22:22205612-22260440 | 1 | 4602 | 0 | 4722 | 0.0002173 | 0 | 0.49356499 | None | case |
| 97 | MTHFD1 | del:chr14:64833333-64888203 | 1 | 4602 | 1 | 4722 | 0.0002173 | 0.00021177 | 0.7435504 | 1.02608129 | case |
| 98 | MTNR1A | dup:chr4:187437316-187505764 | 3 | 4602 | 0 | 4722 | 0.00065189 | 0 | 0.12019589 | None | case |
| 100 | MX1 | del:chr21:42685045-43399914 | 1 | 4602 | 0 | 4722 | 0.0002173 | 0 | 0.49356499 | None | case |
| 101 | MYO6 | del:chr6:76447205-76473071 | 1 | 4602 | 0 | 4722 | 0.0002173 | 0 | 0.49356499 | None | case |
| 102 | NAA15 | del:chr4:140264431-140264431 | 2 | 4602 | 0 | 4722 | 0.00043459 | 0 | 0.24357959 | None | case |
| 103 | NCK1 | dup:chr3:136487559-136606271 | 1 | 4602 | 0 | 4722 | 0.0002173 | 0 | 0.49356499 | None | case |
| 106 | NPY2R | del:chr4:156087185-156160310 | 2 | 4602 | 0 | 4722 | 0.00043459 | 0 | 0.24357959 | None | case |
| 108 | PCBP1 | dup:chr2:70303218-70388670 | 1 | 4602 | 0 | 4722 | 0.0002173 | 0 | 0.49356499 | None | case |
| 109 | PCBP3 | dup:chr21:47323742-47342116 | 3 | 4602 | 1 | 4722 | 0.00065189 | 0.00021177 | 0.30286889 | 3.07958252 | case |
| 110 | PCDHA4 | del:chr5:140227999-140246511 | 3 | 4602 | 1 | 4722 | 0.00065189 | 0.00021177 | 0.30286889 | 3.07958252 | case |
| 111 | PDE1C | del:chr7:32225283-32228302 | 3 | 4602 | 0 | 4722 | 0.00065189 | 0 | 0.12019589 | None | case |
| 113 | PICK1 | del:chr22:38462680-38518731 | 1 | 4602 | 0 | 4722 | 0.0002173 | 0 | 0.49356499 | None | case |
| 114 | PIK3CA | del:chr3:178912662-178941323 | 1 | 4602 | 0 | 4722 | 0.0002173 | 0 | 0.49356499 | None | case |
| 115 | PLA2G7 | del:chr6:46629505-46679303 | 1 | 4602 | 0 | 4722 | 0.0002173 | 0 | 0.49356499 | None | case |
| 116 | PLCB1 | del:chr20:8400086-8412256 | 3 | 4602 | 0 | 4722 | 0.00065189 | 0 | 0.12019589 | None | case |
| 120 | PRDX1 | del:chr1:45936352-46055858 | 1 | 4602 | 1 | 4722 | 0.0002173 | 0.00021177 | 0.7435504 | 1.02608129 | case |
| 121 | PRKCA | del:chr17:64466865-64471675 | 3 | 4602 | 0 | 4722 | 0.00065189 | 0 | 0.12019589 | None | case |
| 122 | PRPSAP1 | del:chr17:74311343-74330638 | 3 | 4602 | 0 | 4722 | 0.00065189 | 0 | 0.12019589 | None | case |
| 124 | PSMC1 | dup:chr14:90621771-90729426 | 1 | 4602 | 0 | 4722 | 0.0002173 | 0 | 0.49356499 | None | case |
| 125 | PSMD1 | del:chr2:232025285-232035793 | 14 | 4602 | 2 | 4722 | 0.00304216 | 0.00042355 | 0.00176964 | 7.20139494 | case |
| 127 | PSMD13 | del:chr11:249132-264390 | 5 | 4602 | 2 | 4722 | 0.00108648 | 0.00042355 | 0.21605246 | 2.56689145 | case |
| 128 | PSME1 | dup:chr14:24587545-24667051 | 2 | 4602 | 0 | 4722 | 0.00043459 | 0 | 0.24357959 | None | case |
| 130 | PXN | dup:chr12:120695141-120747913 | 3 | 4602 | 0 | 4722 | 0.00065189 | 0 | 0.12019589 | None | case |
| 132 | RAB2A | del:chr8:61452046-61526953 | 1 | 4602 | 1 | 4722 | 0.0002173 | 0.00021177 | 0.7435504 | 1.02608129 | case |
| 134 | RANBP1 | dup:chr22:20107729-20117344 | 13 | 4602 | 3 | 4722 | 0.00282486 | 0.00063532 | 0.0092373 | 4.45609065 | case |
| 135 | RAP2A | del:chr13:98076911-98096882 | 1 | 4602 | 0 | 4722 | 0.0002173 | 0 | 0.49356499 | None | case |
| 136 | RCC1 | del:chr1:28742323-28939138 | 3 | 4602 | 1 | 4722 | 0.00065189 | 0.00021177 | 0.30286889 | 3.07958252 | case |
| 137 | RGS12 | dup:chr4:3434336-3436587 | 4 | 4602 | 1 | 4722 | 0.00086919 | 0.00021177 | 0.17949275 | 4.10700304 | case |
| 139 | RPA2 | del:chr1:28107060-28267868 | 1 | 4602 | 0 | 4722 | 0.0002173 | 0 | 0.49356499 | None | case |
| 141 | RPN2 | del:chr20:35740795-35842923 | 1 | 4602 | 0 | 4722 | 0.0002173 | 0 | 0.49356499 | None | case |

FIGURE 15 Continued

|   | A | B | C | D | E | F | G | H | I | J | K |
|---|---|---|---|---|---|---|---|---|---|---|---|
| 143 | RUVBL2 | dup:chr19:49485759-49517212 | 1 | 4602 | 0 | 4722 | 0.0002173 | 0 | 0.49356499 | None | case |
| 145 | RYR2 | del:chr1:237273380-237275393 | 4 | 4602 | 0 | 4722 | 0.00086919 | 0 | 0.05930489 | None | case |
| 146 | S100A6 | del:chr1:153460303-153509890 | 1 | 4602 | 0 | 4722 | 0.0002173 | 0 | 0.49356499 | None | case |
| 147 | SACS | del:chr13:23903792-24224141 | 2 | 4602 | 0 | 4722 | 0.00043459 | 0 | 0.24357959 | None | case |
| 148 | SDC3 | dup:chr1:31375569-31387329 | 1 | 4602 | 0 | 4722 | 0.0002173 | 0 | 0.49356499 | None | case |
| 150 | SERPINB9 | del:chr6:2869032-3174946 | 1 | 4602 | 0 | 4722 | 0.0002173 | 0 | 0.49356499 | None | case |
| 154 | SLC6A3 | dup:chr5:1342714-1395077 | 2 | 4602 | 0 | 4722 | 0.00043459 | 0 | 0.24357959 | None | case |
| 156 | SNRPB2 | dup:chr20:16694602-16739851 | 3 | 4602 | 0 | 4722 | 0.00065189 | 0 | 0.12019589 | None | case |
| 159 | SRC | del:chr20:35942718-36005274 | 1 | 4602 | 0 | 4722 | 0.0002173 | 0 | 0.49356499 | None | case |
| 160 | STRAP | del:chr12:15992222-16094160 | 1 | 4602 | 0 | 4722 | 0.0002173 | 0 | 0.49356499 | None | case |
| 161 | STX12 | del:chr1:28086956-28107059 | 3 | 4602 | 0 | 4722 | 0.00065189 | 0 | 0.12019589 | None | case |
| 162 | SYK | dup:chr9:93557698-93574650 | 1 | 4602 | 0 | 4722 | 0.0002173 | 0 | 0.49356499 | None | case |
| 165 | TCP1 | del:chr6:160152776-160207570 | 1 | 4602 | 0 | 4722 | 0.0002173 | 0 | 0.49356499 | None | case |
| 166 | TEAD3 | dup:chr6:35442397-35465785 | 3 | 4602 | 0 | 4722 | 0.00065189 | 0 | 0.12019589 | None | case |
| 167 | TFAM | del:chr10:60134097-60150445 | 2 | 4602 | 0 | 4722 | 0.00043459 | 0 | 0.24357959 | None | case |
| 169 | TJP1 | del:chr15:29812778-30178613 | 4 | 4602 | 0 | 4722 | 0.00086919 | 0 | 0.05930489 | None | case |
| 173 | TRAF2 | dup:chr9:139776401-139821067 | 6 | 4602 | 1 | 4722 | 0.00130378 | 0.00021177 | 0.05831645 | 6.16318538 | case |
| 174 | TUBA1A | del:chr12:49531458-49586489 | 7 | 4602 | 3 | 4722 | 0.00152108 | 0.00063532 | 0.16138949 | 2.39630033 | case |
| 175 | TUBA3C | dup:chr13:19743860-19748709 | 17 | 4602 | 8 | 4722 | 0.00369405 | 0.0016942 | 0.04695909 | 2.18478735 | case |
| 177 | TXN | dup:chr9:112796113-113112572 | 1 | 4602 | 0 | 4722 | 0.0002173 | 0 | 0.49356499 | None | case |
| 179 | UBQLN4 | del:chr1:155951502-156027550 | 1 | 4602 | 0 | 4722 | 0.0002173 | 0 | 0.49356499 | None | case |
| 180 | VHL | dup:chr3:10180659-10211917 | 1 | 4602 | 1 | 4722 | 0.0002173 | 0.00021177 | 0.7435504 | 1.02608129 | case |
| 181 | YWHAQ | del:chr2:9630231-9758621 | 1 | 4602 | 0 | 4722 | 0.0002173 | 0 | 0.49356499 | None | case |

FIGURE 15 Continued

METHODS OF DIAGNOSING AND TREATING AUTISM

FIELD

Methods for diagnosing and treating autism spectrum disorders are provided.

BACKGROUND

Autism spectrum disorder (ASD) is a range of complex neurodevelopmental disorders characterized by mild to severe social impairments, communication difficulties, and restrictive or repetitive behaviors. ASD, previously known as pervasive developmental disorders (PDD), is an umbrella term that includes various conditions that used to be diagnosed separately such as autistic disorder (or classic autism), Asperger's syndrome, childhood disintegrative disorder, Rett's disorder, pervasive developmental disorder not otherwise specified (PDD-NOS), and social (pragmatic) communication disorder (SCD). (Vieux et al, "Autism Spectrum Disorder: DSM-5 Changes, Epidemiology & Outcomes," *The Carlat Report*, Vol. 11, Issue 6, June 2013.)

ASD occurs in all racial, ethnic, and socioeconomic groups. (Durkin et al., "Socioeconomic inequality in the prevalence of autism spectrum disorder: evidence from a U.S. cross-sectional study," *PLOS One*, 5(7), July 2010.) In 2013, ASD was estimated to occur in 2% of children between the ages of 6 and 17, a significant increase from the estimate of 1.16% in 2007. (see, e.g., Blumberg et. al., *National Health Statistics Reports*, No. 65, Mar. 20, 2013) While it is not known how many adults suffer from ASD, a British study reported that 1.8% adult men and 0.2% adult women have ASD. (Brugha et al., "Epidemiology of autism spectrum disorders in adults in the community in England," *Arch. Gen. Psych.* 68: 459-66, 2011.)

With the increased incidence of ASD comes increased costs to society. The CDC estimates that it costs between $17,000-$21,000 more per year to care for a child diagnosed with ASD as compared to a child not diagnosed with ASD. Medical costs alone for children diagnosed with ASD can be elevated by $4,100-$6,200 per year, with behavioral interventions for children diagnosed with ASD costing $40,000-$60,000 per year. It is estimated that total societal costs of caring for children diagnosed with ASD were over $9 billion in 2011.

Some risk factors and patterns have emerged to assist in diagnosing ASD, and various treatment regimes are often used on a trial and error basis. While there have been improvements in diagnosis and treatment of ASD, there remains a need for consistent diagnosis and treatment of ASD using a genetic approach.

SUMMARY

In accordance with the description, a method for treating autism spectrum disorder (ASD) in patients having at least one CNV in a GRM/mGluR network gene, as shown in FIG. 15, comprising administering a therapeutically effective amount of fasoracetam (NS-105), or member of the piracetam family of nootropic agents, is encompassed. CNVs in GRM/mGluR network genes are sensitive and specific biomarkers for diagnosing ASD. The inventors have identified drug candidates that specifically activate mGluRs, restoring normal neurophysiology in ASD patients having at least one CNV in any of the GRM/mGluR network genes shown in FIG. 15.

In one embodiment, a CNV in at least one of the following GRM/mGluR network genes indicates a diagnosis of ASD: ACAT1, ACAT2, ACP1, ACTR2, ADCY1, ADD1, ADRA2C, ADRBK1, AGAP2, ALDOA, APTX, ARHGAP24, ARL15, BDKRB1, BDKRB2, C1orf116, C4orf3, C7orf25, CA8, CACNA1B, CALB2, CALM1, CAMK2B, CHP, CHRM3, CNPY2, CNR1, COPB2, DCN, DHCR7, DISC1, DSTN, ECHS1, EGFR, ERBB2, ERP44, F2RL2, FKBP3, FURIN, GLP1R, GLP2R, GNA15, GNAI1, GNAI2, GNAI3, GNAO1, GNAQ, GNB2L1, GRB2, GRB7, GRIK1, GRM1, GRM3, GRM5, GRM7, GRM8, GSN, HNRNPA3, HOMER1, HOMER3, HTT, IMPDH2, IQGAP2, ITGB7, ITPR1, LAMA4, LRP2BP, LYAR, LYN, MAP4, MAPK1, MTHFD1, MTNR1A, MX1, MYO6, NAA15, NCK1, NPY2R, PCBP1, PCBP3, PCDHA4, PDE1C, PICK1, PIK3CA, PLA2G7, PLCB1, PRDX1, PRKCA, PRPSAP1, PSMC1, PSMD1, PSMD13, PSME1, PXN, RAB2A, RANBP1, RAP2A, RCC1, RGS12, RPA2, RPN2, RUVBL2, RYR2, S100A6, SACS, SDC3, SERPINB9, SLC6A3, SNRPB2, SRC, STRAP, STX12, SYK, TCP1, TEAD3, TFAM, TJP1, TRAF2, TUBA1A, TUBA3C, TXN, UBQLN4, VHL, and YWHAQ.

Moreover, patients with at least one CNV in a GRM/mGluR network gene will see improvement in ASD upon administration of a therapeutically effective amount of a member of the piracetam family of nootropic agents, as described in F. Gualtieri et al., Curr. Phann. Des., 8: 125-38 (2002). In one embodiment, the treating agent is a pyroglutamide. Details regarding the preparation and formulation of pyroglutamides, which may be used in the practice of this invention, are provided in U.S. Pat. No. 5,102,882 to Kimura et al. In one embodiment the nootropic agent for the treatment of ASD in patients determined to have one or more of the CNVs indicative as set forth in FIG. 15, is (+)-5-oxo-Dprolinepiperidinamide monohydrate (fasoracetam; NS-105).

In one embodiment, the patient has been diagnosed as having pervasive developmental disorder, or one or more conditions selected from autistic disorder (classic autism), Asperger's syndrome, childhood disintegrative disorder, Rett's disorder, pervasive developmental disorder not otherwise specified (PDD-NOS), or social (pragmatic) communication disorder (SCD).

The CNV may be a duplication or deletion.

The ASD may be syndromic or non-syndromic.

In one embodiment, the ASD may be in a patient having 22q11.2 Deletion or Duplication Syndrome, Fetal Valproate Syndrome or Thalidomide Embryopathy.

In one embodiment, the patient has at least two CNVs in a gene selected from the group consisting of ACAT1, ACAT2, ACP1, ACTR2, ADCY1, ADD1, ADRA2C, ADRBK1, AGAP2, ALDOA, APTX, ARHGAP24, ARL15, BDKRB1, BDKRB2, C1orf116, C4orf3, C7orf25, CA8, CACNA1B, CALB2, CALM1, CAMK2B, CHP, CHRM3, CNPY2, CNR1, COPB2, DCN, DHCR7, DISC1, DSTN, ECHS1, EGFR, ERBB2, ERP44, F2RL2, FKBP3, FURIN, GLP1R, GLP2R, GNA15, GNAI1, GNAI2, GNAI3, GNAO1, GNAQ, GNB2L1, GRB2, GRB7, GRIK1, GRM1, GRM3, GRM5, GRM7, GRM8, GSN, HNRNPA3, HOMER1, HOMER3, HTT, IMPDH2, IQGAP2, ITGB7, ITPR1, LAMA4, LRP2BP, LYAR, LYN, MAP4, MAPK1, MTHFD1, MTNR1A, MX1, MYO6, NAA15, NCK1, NPY2R, PCBP1, PCBP3, PCDHA4, PDE1C, PICK1, PIK3CA, PLA2G7, PLCB1, PRDX1, PRKCA, PRPSAP1, PSMC1, PSMD1, PSMD13, PSME1, PXN, RAB2A, RANBP1, RAP2A, RCC1, RGS12, RPA2, RPN2, RUVBL2, RYR2, S100A6, SACS, SDC3, SERPINB9, SLC6A3, SNRPB2, SRC, STRAP, STX12, SYK, TCP1, TEAD3, TFAM, TJP1, TRAF2, TUBA1A, TUBA3C, TXN, UBQLN4, VHL, and YWHAQ.

In one embodiment, the CNVs are detected in any type of biological sample taken from a human patient, including but not limited to, body fluids (including blood, urine, serum, gastric lavage), any type of cell (such as brain cells, white blood cells, mononuclear cells) or body tissue.

Methods for determining whether a patient has a GRM/mGluR network gene CNV include, for example, analyzing the biological sample on a SNP-array, taking into account both LOG-R ratio (intensity data) and BAF (B allele frequency), which assesses allele states. SNP array platforms are commercially available from, for example, Illumina, Affymetrix, and Agilent.

Other methods for determining whether a patient has a GRM/mGluR network gene CNV include, for example, CGH (comparative genomic hybridization), which utilizes intensity data for evaluation of CNVs; whole exome or whole genome sequencing (or targeted sequencing); utilizing specific FISH probes; qPCR; droplet PCR; and taqman probes. Alternatively, certain companies that use proprietary methods for determining the presence or absence of CNVs may be provided samples to be tested for presence of CNVs in GRM/mGluR network genes in accordance with the methods of the invention.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate several embodiments and together with the description, serve to explain the principles described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a schematic of a first-degree interactome of the GABAR-A family highlighting copy number defects enriched in cases vs controls.

FIG. 6 shows a representative enrichment of certain CNVRs across mGluR network of genes. Nodes of the network are labeled with their gene names, with red and green representing deletions and duplications respectively, while grey nodes lack CNV data. Dark and light colors represent enrichment in cases and controls respectively. The genes defining the network are showed as diamonds, while all other genes are shown as circles. Blue lines indicate evidence of interaction.

FIG. 9 shows significant CNVRs in the mGluR network. The table shows the 10 most significant CNVRs for 189 genes with data in the GFIN for the GRM gene family across a European-derived population, as well as the most significant CNVRs harbored by the GRM mGluR receptors themselves.

FIG. 10 shows significant CNVRs across genes in the MXD network in European-derived populations. Where large CNVs span multiple genes, the component gene implicated within the MXD gene family interaction network is bolded.

FIG. 11 shows significant CNVRs across genes in the CALM1 network in European-derived populations.

FIG. 12 shows CNVRs distinguishing cases from controls significant across both European-derived populations (P≤0.0001 by Fisher's exact test) and African-derived populations (P≤0.001). CNVR=copy-number variable region; OR=odds ratio. For each CNVR, the table lists the type (del or dup), the closest gene impacted, the chromosomal band, the approximate size of the defect (Kb), the number of contributing SNPs, the numbers of affected cases and controls, as well as P-value and odds ratio (OR) from Fisher's exact test for across all populations, and subsets of European-derived and African-derived populations. *Genes with an asterisk (*) harbor CNVRs that disrupt their exons of directly, while those without the asterisk are located in the genomic region around the intergenic CNVRs.

FIG. 13 shows significant gene family interaction networks (GFINs) by network permutation testing (Pperm≤0.05) enriched for CNV defects across at least 5% of cases. The table lists the name and size of gene family tested, the number and frequency of network genes enriched in the second degree gene interaction network, the number and frequency of cases harboring defects across the network, the number and frequency of controls harboring defects across the network, the significance of association by Fisher's exact test, the enrichment of CNV defects in cases, and the significance of that enrichment by 1,000 random network permutations.

FIG. 14 shows significant individual gene interaction networks ranked by permutation testing. FIG. 14 lists the name and gene family member tested, the number and frequency of network genes enriched, the number and frequency of cases harbouring defects, the number and frequency of controls harbouring defects, and the significance of association by Fisher's exact test, the odds ratio of the effect size, and the significance of association by random permutation of network while controlling for number of genes tested. Among other highly ranked first degree gene interaction networks were the nuclear receptor co-repressor 1 (NCOR1; Pfisher $\leq$1.11E—06, enrichment=13.37, Pperm$\leq$0.004) and BCL2-associated athanogene 1 (BAG1; Pfisher $\leq$2.18E—04, enrichment=15.40, Pperm$\leq$0.014) networks. NCOR1 is a ranscriptional coregulatory protein that appears to assist nuclear receptors in the downregulation of DNA expression through recruitment of histone deacetylases to DNA promoter regions; it is a principal regulator in neural stem cells. The oncogene BCL2 is a membrane protein that blocks the apoptosis pathway, and BAG1 forms a BCL2-associated athanogene and represents a link between growth factor receptors and antiapoptotic mechanisms. The BAG1 gene has been implicated in age-related neurodegenerative diseases, including Alzheimer's disease.

FIG. 15 shows the raw data described in Examples 1-4. Column A lists the GRM/mGluR network genes that are enriched in patients with ASD. Column B indicates whether the CNV is a duplication or deletion and the genetic start and stop locus. The odds ratio recited in column J recites "none" for any gene where no CNV was found in the control group. In column K, enrichment, the word "case" is indicative of enrichment in CNVs in the associated gene in ASD patients as compared to controls. Finding at least one CNV in any of the genes listed in FIG. 15, Column A, indicates a diagnosis of ASD and implicates treatment with NS-105.

DESCRIPTION OF THE EMBODIMENTS

Definitions

Figure 1:
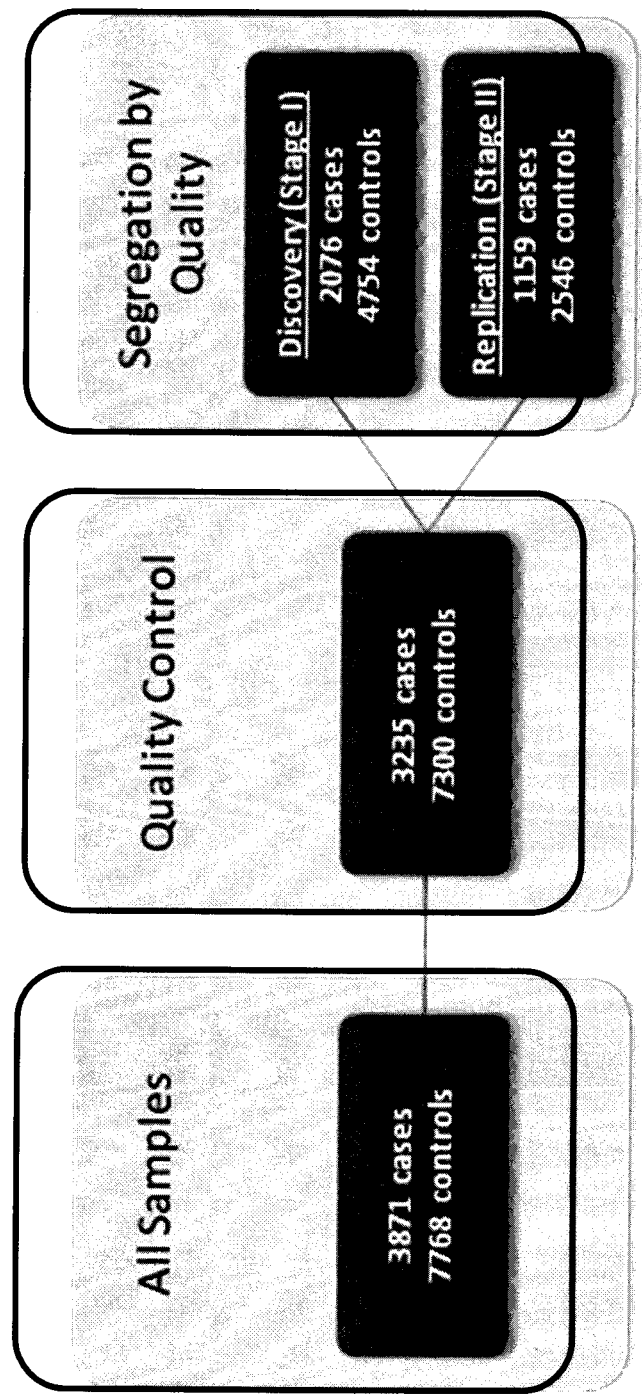
FIG. 1 provides the design of a clinical study. In this two-stage design, 2076 cases vs 4754 controls were used in the discovery cohort (Stage 1), and 1159 cases vs 2546 controls were used for a replication cohort (Stage 2). All samples used passed minimal quality control metrics, but the default quality calls of PennCNV were used to discriminate the discovery cohort (best quality) from the replication cohort (lesser quality.)
Figure 2:
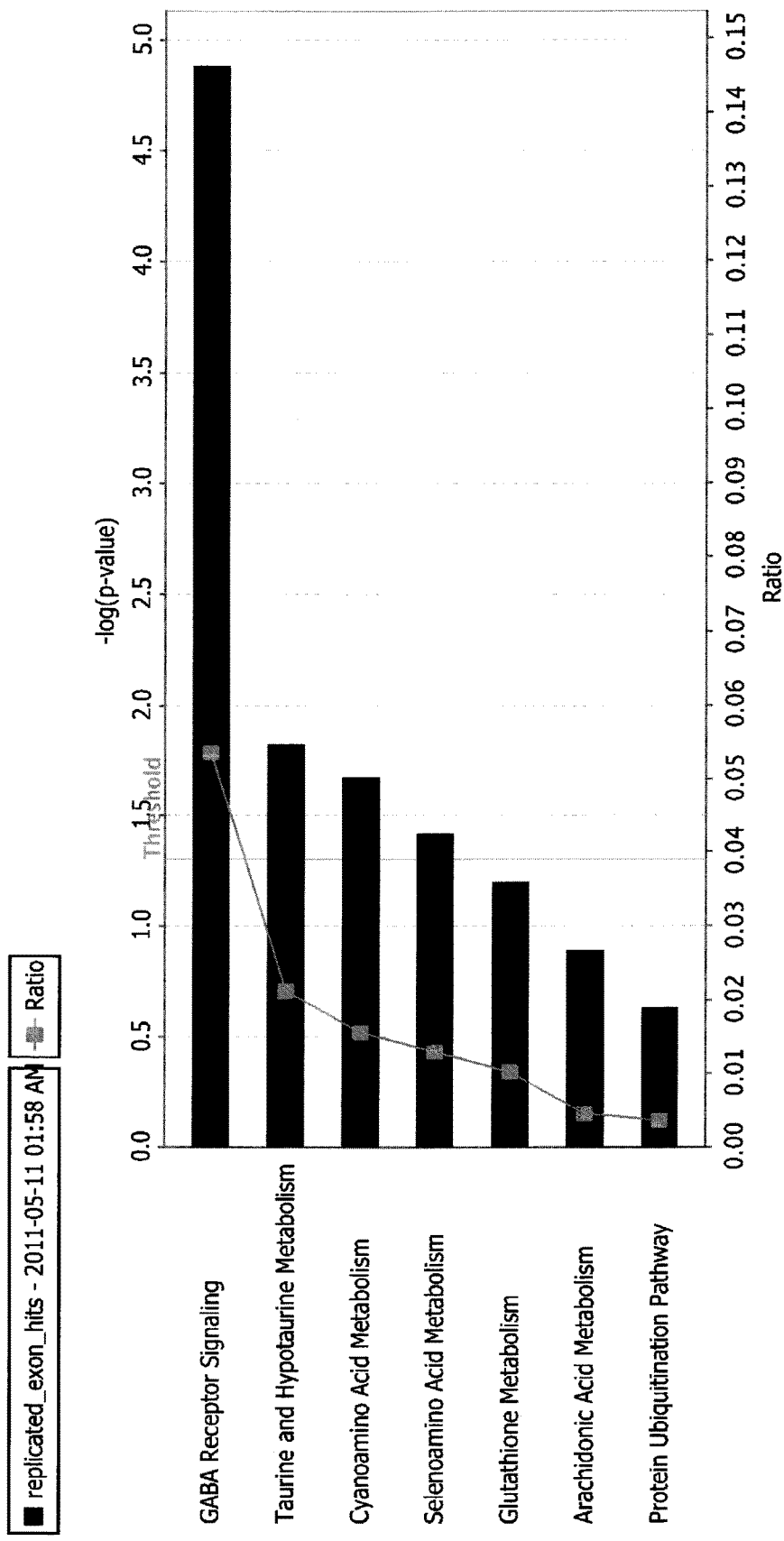
FIG. 2 is a graph showing certain classes of gene pathways, which are disrupted by the ASD-related CNVs disclosed herein. All genes with exons disrupted by replicated CNVs were submitted to Ingenuity to ascertain significance of pathway enrichment.
Figure 4:
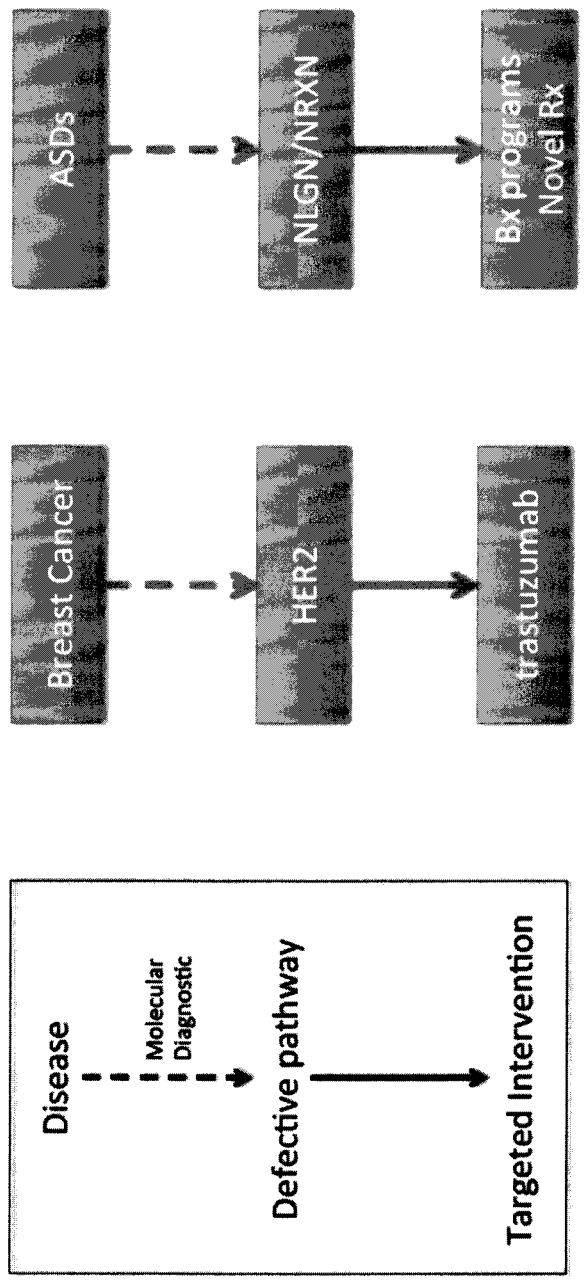
FIG. 4 shows a test and treat model for targeting therapeutics to specific pathways defective in disease. The generic test and treat model is shown in black where a molecular diagnostic is used to genetically define a population with defective pathways that are likely to benefit from a targeted intervention. Examples of trastuzumab as a targeted intervention for HER2 specific breast cancer is shown as well as an extrapolation of behavioral programs and novel therapeutics that are being developed to target ASDs due to defective GABAR-A pathways.

A "copy number variation (CNV)" refers to the number of copies of a particular gene in the genotype of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger (Feuk et al. 2006a). CNVs described herein do not include those variants that arise from the insertion/deletion of transposable elements (e.g., .about.6-kb KpnI repeats) to minimize the complexity of future CNV analyses. The term CNV therefore encompasses previously introduced terms such as large-scale copy number variants (LCVs; Iafrate et al. 2004), copy number polymorphisms (CNPs; Sebat et al. 2004), and intermediate-sized variants (ISVs; Tuzun et al. 2005), but not retroposon insertions.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

"Target nucleic acid" as used herein refers to a previously defined region of a nucleic acid present in a complex nucleic acid mixture wherein the defined wild-type region contains at least one known nucleotide variation, which may or may not be associated with autism. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately 10.sup.-6-fold purification of the native message. Thus, purification of at least one order of magnitude, preferably two or three orders, and more preferably four or five orders of magnitude is expressly contemplated.

The term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any autism specific marker gene or nucleic acid, but does not hybridize to other nucleotides. Also polynucleotide which "specifically hybridizes" may hybridize only to a neurospecific specific marker, such an autism-specific marker shown in the Table contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5 \text{ degrees C.} + 16.6 \text{ Log } [Na^+] + 0.41(\% \; G+C) - 0.63(\% \text{ formamide}) - 600/\#bp \text{ in duplex}$$

As an illustration of the above formula, using $[Na+]=[0.368]$ and 50% formamide, with GC content of 42% and an average probe size of 200 bases, the $T_m$ is 57 degrees C. The $T_m$ of a DNA duplex decreases by 1-1.5 degrees C. with every 1% decrease in homology. Thus, targets with greater than about 75% sequence identity would be observed using a hybridization temperature of 42 degrees C.

The stringency of the hybridization and wash depend primarily on the salt concentration and temperature of the solutions. In general, to maximize the rate of annealing of the probe with its target, the hybridization is usually carried out at salt and temperature conditions that are 20-25 degrees C. below the calculated $T_m$ of the hybrid.

Wash conditions should be as stringent as possible for the degree of identity of the probe for the target. In general, wash conditions are selected to be approximately 12-20 degrees C. below the $T_m$ of the hybrid. In regards to the nucleic acids of the current invention, a moderate stringency hybridization is defined as hybridization in 6×SSC, 5×Denhardt's solution, 0.5% SDS and 100 micro-gram/ml denatured salmon sperm DNA at 42 degree C., and washed in 2×SSC and 0.5% SDS at 55 degree C. for 15 minutes. A high stringency hybridization is defined as hybridization in 6×SSC, 5×Denhardt's solution, 0.5% SDS and 100 microgram/ml denatured salmon sperm DNA at 42 degree C., and washed in 1×SSC and 0.5% SDS at 65 degree C. for 15 minutes. A very high stringency hybridization is defined as hybridization in 6×SSC, 5×Denhardt's solution, 0.5% SDS and 100 micro-gram/ml denatured salmon sperm DNA at 42 degree C., and washed in 0.1×SSC and 0.5% SDS at 65 degrees C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Probes and primers having the appropriate sequence homology which specifically hybridized to CNV containing nucleic acids are useful in the detecting the presence of such nucleic acids in biological samples.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Those skilled in the art will recognize that a nucleic acid vector can contain nucleic acid elements other than the promoter element and the autism specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

"Sample" or "patient sample" or "biological sample" generally refers to a sample, which may be tested for a particular molecule, preferably an autism specific marker molecule, such as a marker shown in the tables and figures provided herein. Samples may include but are not limited to cells, body fluids, including blood, serum, plasma, urine, saliva, tears, pleural fluid and the like.

Methods of Using Autism-Associated CNVS for Diagnosing a Propensity for the Development of Autism and Autistic Spectrum Disorders Autism-related-CNV containing nucleic acids, including but not limited to those listed in the Tables and Figures provided herein, for example in FIG. 15, may be used for a variety of purposes in accordance with the present invention. Autism-associated CNV/SNP containing DNA, RNA, or fragments thereof may be used as probes to detect the presence of and/or expression of autism specific markers. Methods in which autism specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting autism-associated CNVs/SNPs may be conducted on any type of biological sample, including but not limited to body fluids (including blood, urine, serum, gastric lavage), any type of cell (such as brain cells, white blood cells, mononuclear cells) or body tissue. Such detection methods can include for example, southern and northern blotting, RFLP, direct sequencing and PCR amplification followed by hybridization of amplified products to a microarray comprising reference nucleic acid sequences.

Autism-associated CNV/SNP containing nucleic acids, vectors expressing the same, autism CNV/SNP containing marker proteins and anti-Autism specific marker antibodies of the invention can be used to detect autism associated CNVs/SNPs in body tissue, cells, or fluid, and alter autism SNP containing marker protein expression for purposes of assessing the genetic and protein interactions involved in the development of autism.

In some embodiments for screening for autism-associated CNVs, the autism-associated CNV containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art. Alternatively, new detection technologies can overcome this limitation and enable analysis of small samples containing as little as 1 microgram of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify autism-associated CNV marker expression and accordingly, diagnose autism or an autism spectrum disorder.

"Autism" and "Autism Spectrum Disorder" are used interchangeably herein.

As used herein "mGluR network genes" and "GRM/mGluR network genes" are interchangeable.

Kits and Articles of Manufacture

Any of the aforementioned products can be incorporated into a kit which may contain a autism-associated CNV/SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Vectors and probes comprising any of the autism-associated CNV/SNP specific marker polynucleotides described in FIG. 15 are encompassed.

Host cells expressing the autism-associated CNVs/SNPs of the present invention or functional fragments thereof are encompassed.

EXAMPLES

Example 1

A large genome-wide association study (GWAS) of structural variants that disrupt gene family protein interaction networks in patients with autism was performed. Multiple defective networks in the ASDs were found, most notably rare copy-number variants (CNVs) in the metabotropic glutamate receptor (mGluR) signaling pathway in 5.8% of patients with the ASDs. Defective mGluR signaling was found in both ADHD and schizophrenia, two common neuropsychiatric disorders that are highly coincident with the ASDs. Furthermore, other attractive candidates were found such as the MAX dimerization protein (MXD) network that is implicated in cancer, and a Calmodulin 1 (CALM1) gene interaction network that is active in neuronal tissues. The numerous defective gene family interactions found to underlie autism present many novel translational opportunities to explore for therapeutic interventions.

To identify and comprehensively characterize defective genetic networks underlying the ASDs, a large-scale genome association study for copy-number variation (CNVs) enriched in patients with autism was performed. By combining the affected cases from previously published large ASD studies with more recently recruited cases from the Children's Hospital of Philadelphia, one of the largest searches for rare pathogenic CNVs in ASDs to date was executed. In sum, 6,742 genotyped samples from patients with the ASDs were compared with those from 12,544 neurologically normal controls recruited at The Children's Hospital of Philadelphia (CHOP).

These cases were each screened by neurodevelopmental specialists to exclude patients with known syndromic causes for autism. Genotyping was performed for the vast majority of the ASD cases as well as all the controls. After cleaning the data to remove sample duplicates and performing standard QC for CNVs, the continental ancestry of 5,627 affected cases and 9,644 disease-free controls was inferred using a training set defined by populations from HapMap 3 and the Human Genome Diversity Panel (Table 1). Using this QC criteria, it was estimated that the sensitivity and specificity of calling CNVs is ~70% and 100%, respectively, across 121 different genomic regions assayed by PCR. Across all ethnicities, there was an increased burden of CNVs in cases versus controls, a statistically significantly difference ($P \leq 0.001$) in the larger European (63.3 versus 54.5 Kb, respectively) and African-derived (70.4 versus 48.0 Kb, respectively) populations.

TABLE 1

Distribution of CNVs across samples and estimated ancestry.

| Continent ancestry | Case | Control | Total |
|---|---|---|---|
| Europe | | | |
| Number of samples | 4,602 | 4,722 | 9,324 |
| *CNV burden (Kb) | 63.3 | 54.5 | |
| Africa | | | |
| Number of samples | 312 | 4,169 | 4,481 |
| *CNV burden (Kb) | 70.4 | 48.0 | |
| America | | | |
| Number of samples | 485 | 276 | 761 |
| CNV burden (Kb) | 59.1 | 58.4 | |
| Asia | | | |
| Number of samples | 201 | 350 | 551 |
| CNV burden (Kb) | 56.1 | 54.1 | |
| Other | | | |
| Number of samples | 27 | 127 | 154 |
| CNV burden (Kb) | 51.5 | 49.4 | |
| All Ethnicities | | | |
| Number of samples | 5,627 | 9,644 | 15,271 |
| *CNV burden (Kb) | 63.0 | 51.7 | |

Referring to Table 1, CNV=copy-number variation. The table shows the distribution of cases, controls and CNV coverage across estimated continental ancestry. For groups of cases and controls across estimated ancestries, the table lists the numbers of subjects that passed quality control and their group-wise CNV burden, defined as the average span of CNVs in Kb for each group.

Referring to Table 1, *Statistically significant $P \leq 0.01$ by PLINK permutation test) differences in CNV burden are marked with an asterisk (*).

Example 2

A search was performed for pan-ethnic CNV regions (CNVRs) discovered in the European-derived data set (4,602 cases versus 4,722 controls; $P \leq 0.0001$ by Fisher's exact test) and replicated in an independent ASD data set of African ancestry (312 cases versus 4,169 controls; $P \leq 0.001$ by Fisher's exact test) with subsequent measurement of overall significance across the entire multi-ethnic discovery cohort (5,627 cases versus 9,644 controls) for maximal power (FIG. 5, FIG. 10).

Figure 5:
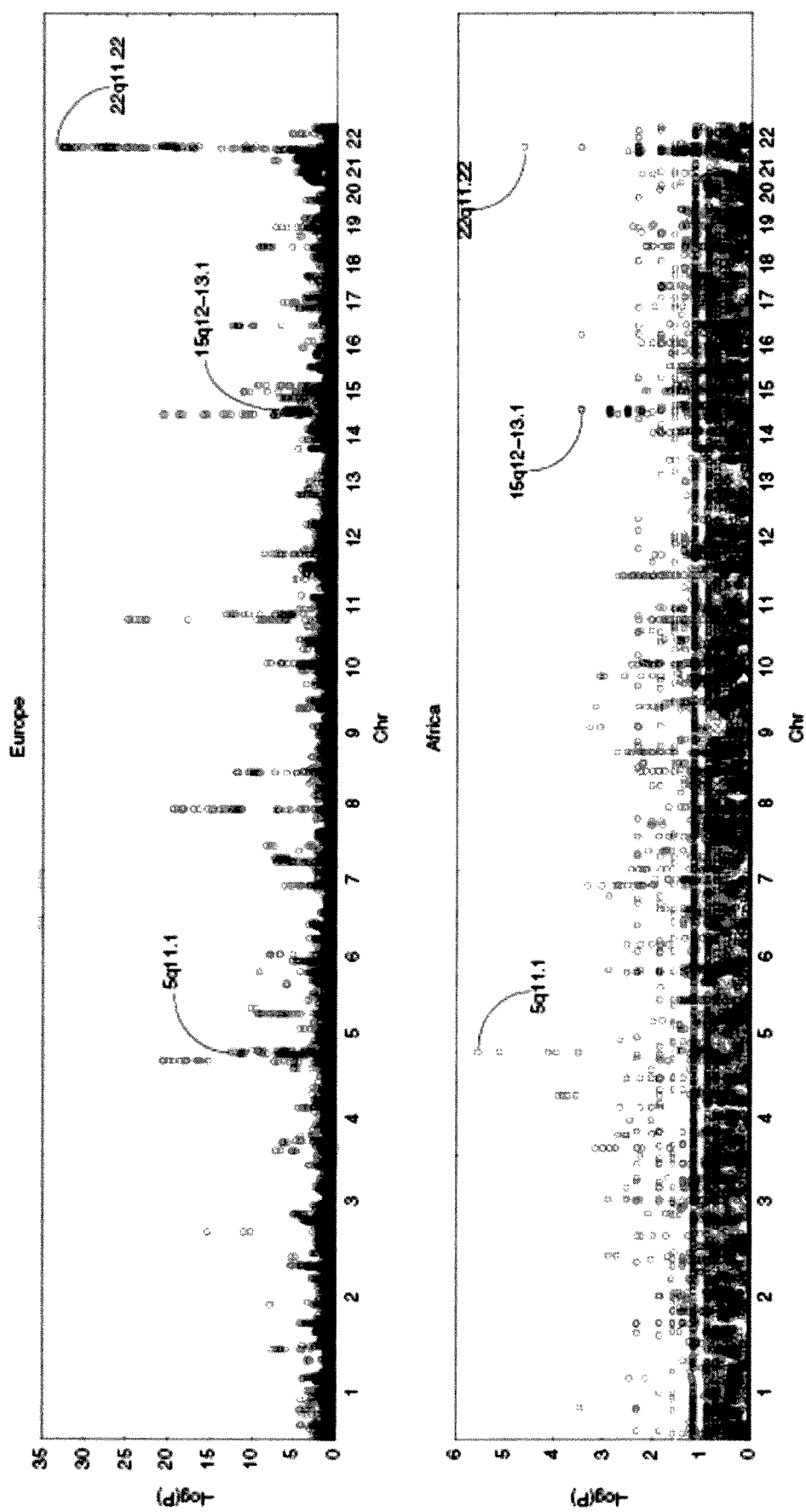
FIG. 5 shows certain identified genetic marker CNVRs by GWAS predictive of ASDs in European-derived or African-derived populations. The Manhattan plots show the −log 10 transformed P value of association for each CNVR along the genome. Adjacent chromosomes are shown. The regions discovered in Europeans (P 0.0001) that replicated in Africans (P<=0.001) are highlighted with black arrows labeled by chromosome band. GWAS of 4,634 cases vs 4,726 controls in Europeans is shown on top and GWAS of 312 cases vs 4,173 controls in Africans is shown below.

FIG. 5 shows the significance of CNVRs by GWAS of ASDs in European-derived or African-derived populations. The Manhattan plots show the −log 10 transformed P-value of association for each CNVR along the genome. Adjacent chromosomes are shown in alternating red and blue colors. The regions discovered in Europeans (P≤0.0001) that replicated in Africans (P≤0.001) are highlighted with black arrows labeled by chromosome band. GWAS of 4,634 cases versus 4,726 controls in Europeans is shown on top and GWAS of 312 cases versus 4,173 controls in Africans is shown below.

On the basis of these selection criteria, two large well-known ASD risk loci emerged that harbored multiple duplications in the Prader Willi/Angelman syndrome (15q11-13) critical region, and multiple deletions were detected in the DiGeorge syndrome (22q11) critical region, albeit notably smaller than the 22q11 deletion syndrome. A third locus harboring deletions in polyADP-ribose polymerase family 8 (PARP8) on chromosome 5q11 was also discovered. PARP8 has previously been identified as associated with the ASDs in a Dutch population but it has not previously been described for its pan ethnic distribution across European-derived and African-derived populations.

Example 3

The genetic interaction networks derived from gene families with members localized to the Prader Willi/Angelman syndrome (15q11-13) critical region, the DiGeorge syndrome (22q11) critical region, and the novel PARP8 (5q11) region were examined using a method previously applied to ADHD; however, hardly any of the most significant genes harboring significant CNVRs clustered within gene families. Consequently, the search for gene family interaction networks (GFINs) was broadened to search the entire genome for GFINs with CNVs enriched in autism. For every gene family, a GFIN was defined as the genetic interaction network spawned by its multiple duplicated members. Standard HUGO gene names were used to define 1,732 GFINs across which were searched for enrichment of network defects associated with the ASDs. However, because there is an a priori excess of CNV burden in ASD cases over disease-free controls (Table 1), larger GFINs are expected to display significant enrichment of case defects by virtue solely of their increased size and complexity. Therefore, for each GFIN, a network permutation test of case enrichment was used across 1,000 random sets of networked genes to control for the GFIN size and complexity. With this approach, network defects associated with the ASDs were identified by minimizing statistical artifact derived from any a priori excessive CNV burden in cases over controls, as well as other unknown biases that may be inherent in the human interactome data that were mined.

Out of 1,732 GFINs, the network permutation test was used to rank 1,557 GFINs with defined CNVs for enrichment of genetic defects in the ASDs. Among the top GFINs (FIG. 13) was the metabotropic glutamate receptor (mGluR) pathway defined by the GRM family of genes that impacts glutamatergic neurotransmission. The GRM family contains eight members, all of which were defined in the human interactome to cumulatively spawn a GFIN of 279 genes (FIG. 6). Across this GFIN for the GRM family of genes, we found CNV defects in 5.8% of European-derived ASD cases (265/4,602) versus only 3% of ethnically matched controls (153/4,722), a 1.8-fold enrichment of frequency (PFisher≤2.40E-09). By 1,000 random network permutations, we found this excess of enrichment across cases in the mGluR pathway to also be statistically significant (Pperm≤0.05). In addition, 69.2% (124/181) of the informative genes within our mGluR network showed an excess of CNVs among cases. However, the component genes that harbor the most significant CNVRs contributing to this overall network significance reveal that the duplicated mGluR genes themselves (GRM1, GRM3, GRM4, GRM5, GRM6, GRM7 and GRM8) fail to achieve significance individually, although there is a trend for an excess of CNV defects across a specific subset of mGluR receptors (GRM1, GRM3, GRM5, GRM7, GRM8) that is unique to cases (FIG. 9).

FIG. 6 shows enrichment of optimal CNVRs across mGluR network of genes. Nodes of the network are labeled with their gene names, with red and green representing deletions and duplications, respectively, while grey nodes lack CNV data. Dark and light colors represent enrichment in cases and controls, respectively. The genes defining the network are shown as diamonds, while all other genes are shown as circles. Blue lines indicate evidence of interaction.

Example 4

Many large studies of CNVs implicate genes within the glutamatergic signaling pathway in the aetiology of the ASDs, and SNP and CNV duplications of GRM8 have been reported in association with the ASDs before in humans. Moreover, a recent functional study demonstrated that in mouse models of tuberous sclerosis and fragile X, two different forms of syndromic autism, the autistic phenotype was ameliorated by modulation of GRM5 in opposite directions for each syndrome, which suggests that GRM5 functional activity is central in defining the axis of synaptopathophysiology in syndromic autism. The GRM network findings herein implicate rare defects in mGluR signalling also contribute to the ASDs outside of fragile X and tuberous sclerosis, and functional mGluR synaptopathophysiology may be initiated from many dozens if not hundreds of defective genes within the mGluR pathway that may account for as much as 6% of the endophenotypes of the ASDs (FIG. 13).

In addition, the importance of mGluRs in ADHD, a highly co-incident neuropsychiatric disorder within the autism spectrum, has been demonstrated. However, in contrast to ADHD where defects within the mGluR receptors themselves (GRMs) were among the most significant copy-number defects contributing to the overall network significance, it was found that in the ASDs defects of component GRMs contributed only modestly to the overall significance of the mGluR pathway. Nonetheless, the defects within GRM1, GRM3, GRM5, GRM7 and GRM8 that were identified as unique to cases and thus enriched are the same GRMs that were identified as being pathogenic in ADHD and may impact glutamatergic signaling.

Among the most highly ranked GFINs by permutation testing, the MAX dimerization protein (MXD) GFIN (PFisher enrichment≤3.83E-23, Pperm≤0.042) was the most enriched. The MXD family of genes encode proteins that interact with MYC/MAX network of basic helix-loop-helix leucine zipper (bHLHZ) transcription factors that regulate cell proliferation, differentiation and apoptosis (MIM 600021); MXD genes are important candidate tumour suppressor genes as the MXD-MYC-MAX network is dysregulated in various types of cancer. Interestingly an epidemiological link between autism and specific types of cancer has been reported, and anticancer therapeutics were recently shown to modulate ASD phenotypes in the mouse through regulation of synaptic NLGN protein levels. Within the component genes contributing to the MXD GFIN significance, duplications in PARP10 (P≤4.06E-11, OR=2.04) and UBE3A (1.50E-06, OR=inf) are the most significantly enriched (FIG. 12). It is notable that PARP8 was found to be significant across ethnicities as described earlier (FIG. 12), and the importance of structural defects in UBE3A in the ASDs was previously described.

Other notable significant GFINs uncovered were POU class 5 homeobox (POU5F) GIFN (PFisher≤2.96E-17, enrichment=2.3, Pperm≤0.008, and the SWI/SNF related, matrix associated, actin-dependent regulator of chromatin, subfamily c (SMARCC) GFIN (PFisher enrichment≤1.22E-09, enrichment=1.9, Pperm≤0.035). The POU5F family of genes encodes for transcription factors containing a POU homeodomain, and their role has been demonstrated in embryonic development, especially during early embryogenesis, and it is necessary for embryonic stem cell pluripotency. Component genes of the SMARCC gene family are members of the SWI/SNF family of proteins, whose members display helicase and ATPase activities and which are thought to regulate transcription of certain genes by altering the chromatin structure around those genes. Most interestingly, the KIAA family of genes ranked among the top GFINs (PFisher enrichment≤3.12E-23, enrichment=1.6, Pperm≤0.040). KIAA genes have been identified in the Kazusa cDNA sequencing project and are predicted from novel large human cDNAs; however, they have no known function.

Some component members of gene families may contribute disproportionately to the significance of a GFIN because they are highly connected to interacting gene partners that are enriched for CNV defects in ASD. Therefore, the 1,732 gene families were decomposed into their 15,352 component duplicated genes of which 1,218 had defined networks with data to test for significance by genome-wide network permutation. The calmodulin 1 (CALM1) gene interaction network ranked highest by network permutation testing of case enrichment for CNV defects across 1,000 random gene networks (FIG. 7, FIG. 14) and represents a novel and attractive candidate gene for the ASDs. Across the CALM1 network, CNV defects were found in 14/4,618 cases versus only 1/4726 controls (Pfisher ≤4.16E-04, enrichment=14.37, Pperm≤0.002), and these defects were distributed such that 90% (9/10) of genes that harbored CNVs in the CALM1 interactome were enriched in cases. Closer inspection of the most significant CNVR contributing to the CALM1 network significance (FIG. 11) revealed that no single gene was significant on its own; instead, with the exception of only one gene (PTH2R), each contributing CNVR tagged highly penetrant rare defects unique to cases. Calmodulin is the archetype of the family of calcium-modulated proteins of which nearly 20 members have been found. Calmodulin contains 149 amino acids that define four calcium-binding domains used for Ca2+-mediated coordination of a large number of enzymes, ion channels and other proteins including kinases and phosphatases; its functions include roles in growth and cell cycle regulation as well as in signal transduction and the synthesis and release of neurotransmitters [MIM 114180].

Figure 7:
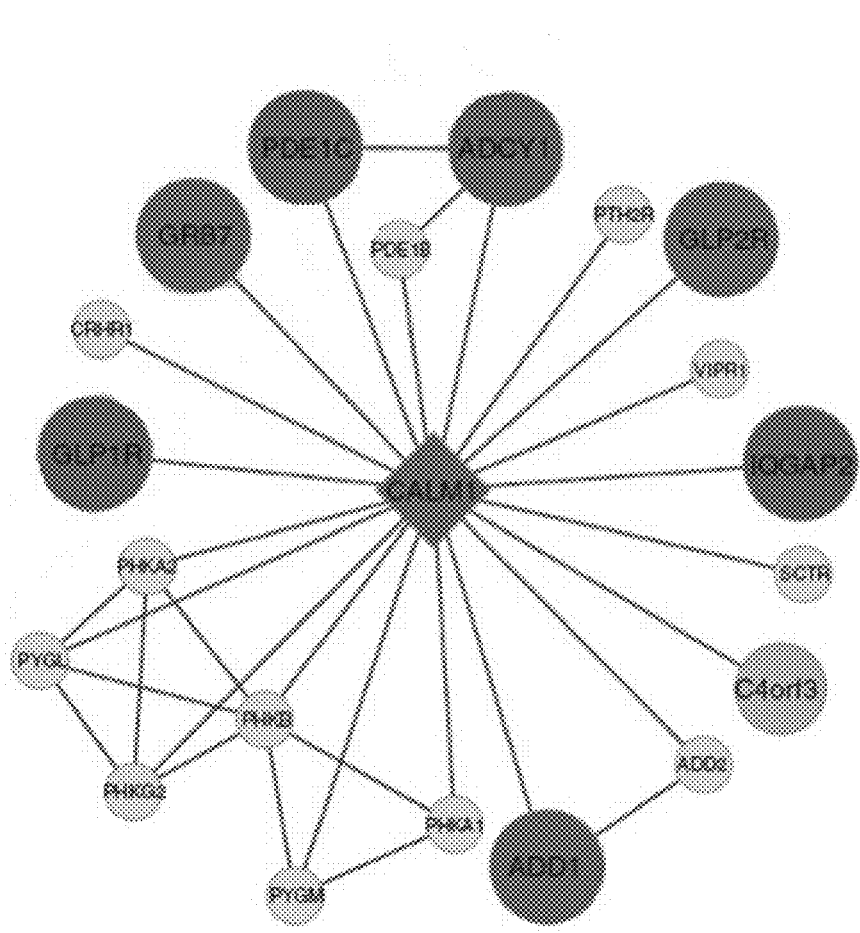
FIG. 7 shows a representative graph of enrichment of optimal CNVRs across the CALM1 network. The first degree directed interaction network defined by CALM1 is shown.

FIG. 7 shows the enrichment of optimal CNVRs across CALM1 network. The first degree-directed interaction network defined by CALM1 is shown.

The comprehensive, unbiased analytical approach described herein has identified a diverse set of specific defective biological pathways that contribute to the underlying aetiology of the ASDs. Among GFINs robustly enriched for structural defects, the most enriched was that of the MXD family of genes that has been implicated in cancer pathogenesis, thereby providing concrete genetic defects to explore the reported coincidence of specific cancers with the ASDs. The most highly ranked component duplicated gene interaction network involves defects in CALM1 and its multiple interacting partners that are important in regulating voltage-independent calcium-activated action potentials at the neuronal synapse. Moreover, there was significant enrichment for defects within the GFIN for GRM that defines the mGluR pathway. While specific mGluR gene family members have been shown to underlie syndromic ASDs, these findings suggest that rare defects in mGluR signaling also contribute to idiopathic autism across the entire GFIN for GRM genes.

Given the unmet need for better treatment for neurodevelopmental diseases, the functionally diverse set of defective genetic interaction networks reported herein presents attractive genetic biomarkers to consider for targeted therapeutic intervention in ASDs and across the neuropsychiatric disease spectrum.

Methods Applicable to Examples 1-4

The majority of cases (5,049 of 6,742) and all controls (12,544) were genotyped with genome-wide coverage using the Infinium II platform across various iterations of the HumanHap BeadChip with 550 K, 610 K, 660 K and 1 M markers by the Center for Applied Genomics at The Children's Hospital of Philadelphia (CHOP). There were 1,693 cases genotyped by the AGP consortium. All cases and ~\n50% of controls were re-used from previously published large ASD studies. All cases were diagnosed by ADI-R/ADOS and fulfilled standard criteria for ASDs. Duplicate samples were removed by selecting unique samples with the best quality (based on genotyping statistics used to QC samples) from clusters defined by single linkage clustering of all pairs of samples with high pairwise identity by state measures (IBS≤0.9) across 140 K non-correlated SNPs. Ethnicity of samples was inferred by a supervised k-means classification (k=3) of the first 10 eigenvectors estimated by principal component analysis across the same subset of 140 K non-correlated SNPs. We used HapMap 3 and the Human Genome Diversity Panel samples with known continental ancestry to train the k-means classifier implemented by the R Language for Statistical Computing.

CNV Inference and Association

CNVs with the PennCNV algorithm, which combines multiple values, including genotyping fluorescence intensity (Log R Ratio), population frequency of SNP minor alleles (B-allele frequency) and SNP spacing were called into a hidden Markov model. The term 'CNV' represents individual CNV calls, whereas 'CNVR' refers to population-level variation shared across subjects. Quality control thresholds for sample inclusion in CNV analysis included a high call rate (call rate ≥95%) across SNPs, low s.d. of normalized intensity (s.d. ≤0.3), low absolute genomic wave artifacts (|GCWF|≤0.02) and low numbers of CNVs called (#CNVs≤100). Genome-wide differences in CNV burden, defined as the average span of CNVs, between cases and controls and estimates of significance were computed using PLINK. CNVRs were defined based on the genomic boundaries of individual CNVs, and the significance of the difference in CNVR frequency between cases and controls was evaluated at each CNVR using Fisher's exact test.

Gene Family Interaction Networks Definition and Association

Previous work on ADHD was extended here to rank all GFINs by a network permutation test. Specifically, using merged human interactome data from three different yeast two hybrid generated data sets accessed through the Human Interactome Database, the directed second-degree gene interaction network was defined for all gene families just as was done for the sole metabotropic glutamate receptor gene family network in ADHD. Specifically, GFIN was used to refer to these gene family-derived interaction networks. In sum, 2,611 gene families were found with at least two members based on official HUGO gene nomenclature, and generated 1,732 GFINs using. For 1,557 GFINs with defined CNVs an odds ratio was calculated of cumulative network enrichment over all genes harboring CNVs within the network. Moreover, for each GFIN, its enrichment was quantified by a permutation test of 1,000 second-degree gene interaction networks derived from a random set of N genes, where N is the number of members of a given gene family. Because the CNVs focused on are so rare, there is relatively not enough power to achieve significance by permutation testing after correcting for multiple GFIN tests. However, all GFINs are reported in order of their nominal/marginal significance.

Experimental Validation of CNVs

Significant CNVRs that were identified were validated using commercially available qPCR Taqman probes run on the ABI GeneAmp 9700 system from Life Technology. FIG. 9 lists 251 reactions that were tested using 121 different genomic probes across 85 different samples for which DNA was available. For deletions, sensitivity=0.65, specificity=1.00, NPV=1.00 and PPV=0.88. For duplications, sensitivity=0.68, specificity=0.99, NPV=0.94 and PPV=0.91.

Conclusions

The data presented herein is evidence that ASD can be diagnosed after recognition of at least one CNV in an mGluR network gene selected from the group consisting of ACAT1, ACAT2, ACP1, ACTR2, ADCY1, ADD1, ADRA2C, ADRBK1, AGAP2, ALDOA, APTX, ARHGAP24, ARL15, BDKRB1, BDKRB2, C1orf116, C4orf3, C7orf25, CA8, CACNA1B, CALB2, CALM1, CAMK2B, CHP, CHRM3, CNPY2, CNR1, COPB2, DCN, DHCR7, DISC1, DSTN, ECHS1, EGFR, ERBB2, ERP44, F2RL2, FKBP3, FURIN, GLP1R, GLP2R, GNA15, GNAI1, GNAI2, GNAI3, GNAO1, GNAQ, GNB2L1, GRB2, GRB7, GRIK1, GRM1, GRM3, GRM5, GRM7, GRM8, GSN, HNRNPA3, HOMER1, HOMER3, HTT, IMPDH2, IQGAP2, ITGB7, ITPR1, LAMA4, LRP2BP, LYAR, LYN, MAP4, MAPK1, MTHFD1, MTNR1A, MX1, MYO6, NAA15, NCK1, NPY2R, PCBP1, PCBP3, PCDHA4, PDE1C, PICK1, PIK3CA, PLA2G7, PLCB1, PRDX1, PRKCA, PRPSAP1, PSMC1, PSMD1, PSMD13, PSME1, PXN, RAB2A, RANBP1, RAP2A, RCC1, RGS12, RPA2, RPN2, RUVBL2, RYR2, S100A6, SACS, SDC3, SERPINB9, SLC6A3, SNRPB2, SRC, STRAP, STX12, SYK, TCP1, TEAD3, TFAM, TJP1, TRAF2, TUBA1A, TUBA3C, TXN, UBQLN4, VHL, and YWHAQ (also shown in FIG. 15).

The CNVs in these genes are sensitive and specific biomarkers for selecting and treating ADHD due to defective mGluR pathways. Furthermore, the present inventors have identified drug candidates that specifically activate the mGluRs, potentially restoring normal neurophysiology in ASD patients with mutations in any of the mGluR network genes, as shown in FIG. 15.

For example, compounds which may be administered in implementing the test and treat paradigm described herein include the piracetam family of nootropic agents, as described in F. Gualtieri et al., Curr. Phann. Des., 8: 125-38 (2002). More preferably, the treating agent is a pyroglutamide. Details regarding the preparation and formulation of pyroglutamides, which may be used in the practice of this invention, are provided in U.S. Pat. No. 5,102,882 to Kimura et al. A particularly preferred agent for the treatment of ASD in patients determined to have one or more of the CNVs indicative as set forth in FIG. 15, is (+)-5-oxo-Dprolinepiperidinamide monohydrate (NS-105).

Example 5

The Role of mGluR Copy Number Variation in Genetic and Environmental Forms of Syndromic Autism Spectrum Disorder Abnormal signaling mediated through mGluR5 is involved in the pathophysiology of Autism Spectrum Disorder (ASD) in Fragile X Syndrome and Tuberous Sclerosis. However, the role of other mGluR associated network/signaling genes in syndromic ASD is unknown. To determine whether copy number variants (CNV'S) are enriched in syndromic ASD, microarrays were used to identify mGluR network CNV's in children with ASD. We set out to determine 1) whether rate of syndromic features vary between children with ASD with and without CNV's in mGluR network genes; and 2) whether "second hits" in mGluR network genes occur more often in children with ASD in children with 22q11.2 Deletion Syndrome (who all have haplo insufficiency of RANBP1, an mGluR network gene in the 22q11.2 region.

Individuals in our biorepository with parental report of ASD (n=6,452) were screened for parental consent to access clinical evaluations in the Electronic Health Record at the Children's Hospital of Philadelphia (n=539). Our syndromic comparison cohort included children with 22q11.2 Deletion Syndrome with full access to past medical and neuropsychological evaluations (n=75), including those with diagnosis of ASD (n=25) and those with no concern for ASD (n=50).

Patient categorization (syndromic vs nonsyndromic) was done via blinded medical chart review in all mGluR positive and 100 randomly selected mGluR negative cases.

Our results, explained further herein show that 11.5% of ASD had mGluR CNV's vs. 3.2% in healthy controls (p<0.001). Syndromic ASD was more prevalent in children with mGluR CNVs (72% vs 16%, p<0.001). A comparison cohort of children with 22q11.2 Deletion Syndrome (n=25 with ASD, n=50 without ASD), all haplo-insufficient for mGluR network gene RANBP1, was evaluated to determine whether "second hits" in mGluR network genes confer additional risk for ASD. 20% with 22q11.2DS+ASD had "second hits" in mGluR signaling genes vs 2% in 22q11.2DS-ASD (p<0.014). Conclusions: We propose that altered RANBP1 expression may provide a mechanistic link between ASD in 22q11.2DS, Thalidomide Embryopathy and Fetal Valproate Syndrome, providing a link for seemingly unrelated genetic and environmental forms of ASD.

The results suggest that CNV's in mGluR network genes, previously implicated in altered neurological development in Fragile X Syndrome and Tuberous Sclerosis, may link many other genetic and environmental forms of Autism Spectrum Disorder. As discussed in the previous examples, Autism Spectrum Disorder (ASD) occurs in approximately 1/88 individuals and is characterized by impairment in social communication and repetitive interests and activities. Approximately 20% of cases occur in the context of an identifiable syndrome. Genetic syndromes with ASD are heterogeneous, including cytogenetically visible chromosomal alterations (e.g. Trisomy 21), microdeletion and microduplication syndromes (e.g. 22q11.2 deletion syndrome [22q11.2DS]; 22q11.2 duplication syndrome [22q11.2DupS]), and monogenic disorders (e.g. Fragile X Syndrome [FXS], Tuberous Sclerosis [TS]). In addition, prenatal exposure to thalidomide, valproic acid, misoprostol, ethanol and maternal rubella infection, have been associated with an elevated risk of ASD.

The mechanism for the development of ASD in most forms of idiopathic and syndromic forms of ASD remains elusive. Recently, signaling through metabotropic glutamate receptor 5 (mGluR5) has been implicated in the development of ASD in FXS and TS. In FXS, abnormal production of Fragile X Mental Retardation Protein (FMRP) removes normal inhibition of signaling through the mGluR pathway. Tuberous Sclerosis leads to over inhibition of signaling. Auerbach and colleagues (2011) demonstrated abnormal synaptic learning and atypical behavior in mouse models of FXS and TS, and reversed these effects by breeding the two strains together—mice harboring both mutations had normal mGluR signaling, and learning and behavior that was indistinguishable from control mice. Other studies have demonstrated normalization of learning and behavior in Fragile X mice by administration of an mGluR5 antagonist. In addition to elucidating the mechanism for cognitive and behavioral differences in FXS and TS, these studies suggest a promising avenue for pharmacological treatment. To determine whether additional forms of syndromic ASD may share a similar mechanism (through disruption of the mGluR gene network), we analyzed DNA from 539 children with ASD (not filtered for comorbid genetic syndrome) followed at the Children's Hospital of Philadelphia.

The following materials and methods are provided to facilitate the practice of Example 5.

Participants: Phenotypic data for patients with ASD as reported on parental health questionnaires from our biorepository (n=6,452) were evaluated to identify patients who received clinical assessment at the Children's Hospital of Philadelphia and agreed to Electronic Health Record chart review. DNA from these cases (n=539) were selected for further phenotypic and genotypic analysis. Children were recruited for inclusion in the general Center for Applied Genomics biorepository when they were getting blood drawn for another purpose at The Children's Hospital of Philadelphia, so there is an overrepresentation of children with at least one medical problem in this patient cohort. The parents of all patients gave consent for participation in the study, which was approved by the Institutional Review Board at the Children's Hospital of Philadelphia (IRB 06-004886).

Chart Review: Subject selection and randomization process: All patients with an mGluR CNV (n=62) and 100 patients without mGluR CNV were randomly selected for chart review. This procedure was selected to ensure that all patients with mGluR CNV received detailed chart review with an adequately sized comparison cohort. A three-step process was done to ensure blinded chart review. The selection of the 162 charts was done by a geneticist with access to CNV data but without access to the Electronic Health Record (CK). Another author who had no access to CNV data nor the Electronic Health Record blinded and randomized the patient ID's (RTS). Finally, a physician with access to the Electronic Health Record but blinded to mGluR status (TLW) reviewed charts for documentation of ASD diagnosis and presence of other medical comorbidities.

ASD: Charts were reviewed to confirm a diagnosis of ASD and also to determine medical comorbidities for each patient. Diagnosis of ASD was confirmed in the chart, but as this was a retrospective chart review, gold-standard research instruments (e.g. Autism).

Figure 8:
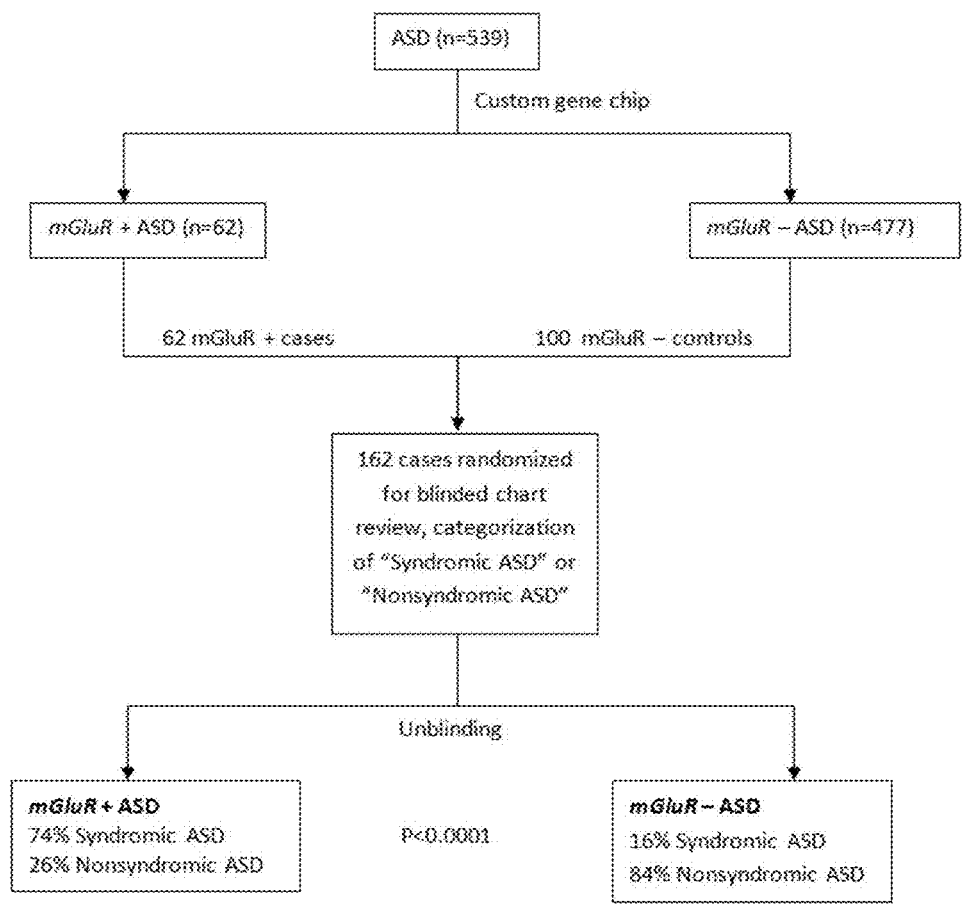
FIG. 8 shows a diagram of representative study design. Results from this study show that children with ASD and gene changes in mGluR network (mGluR+ASD) were more likely to have Syndromic ASD as compared to children with ASD without abnormalities of mGluR network genes (mGluR-ASD). P<0.0001.

Medical Comorbidities: Structural birth defects, genetic testing and medical conditions were recorded for each patient. Cases were categorized as "Syndromic ASD" if they had ASD and presence of a medical condition or structural birth defect (e.g. cleft palate) that occurs in less than 1% of the general population. This criteria was established to define a subset of patients whose ASD and other medical problems would be highly unlikely to occur coincidentally—With a baseline rate of ASD at 1/88 and a medical condition that occurs in <1% of the general population, the compound likelihood of both occurring by chance would be approximately 0.001%. See FIG. 8.

Genotyping Arrays and CNV Calling: DNA from subjects with ASD were each genotyped on the Human610-Quad or HumanHap550 SNP arrays from Illumina. For 22q11 DS cohorts, subjects were typed either on Illumina SNP arrays (Human610-Quad v1.0 or HumanHap550) or Affymetrix 6.0 SNP arrays. Clustering and SNP calling was performed using GenomeStudio (Illumina) to generate normalized intensity (i.e. Log-R ratio, or LRR) and B-allele frequencies (BAF). CNV calling was performed using the PennCNV algorithm [PMID: 17921354] following waviness correction [PMID: 18784189]. In brief, PennCNV uses a hidden Markov model (HMM) that incorporates information from LRR, BAF, as well as features of the array (e.g. distance between neighboring SNPs) to detect CNVs.

CNV Quality Control: Samples with SNP arrays of poor quality were excluded from CNV calling, since typically the proportion of false positives increases considerably for these samples. Those samples where the genotyping call rate>96%, standard deviation of LRR (LRR sd)<0.4, GC-wave factor (GCWF) is between –0.2 and 0.2 after waviness correction, and total number of CNV calls for the sample <100 were included in analysis.

CNV Annotation: For syndromic ASD regions, genomic coordinates were those described by Betancur [PMID: 21129364]. The GRM/mGluR network generated by Cytoscape from the Human Interactome database was described by Elia et al. [PMID: 22138692] using UCSC Genome Browser definitions for gene coordinates (UCSC genes). This network from Cytoscape was used to define mGluR+vs. mGluR-subsets. For 22q11 DS cohort analysis, additional GRM/mGluR network genes were identified based on 1st degree interaction network of the eight GRM genes using the program Ingenuity Pathway Analysis (Ingenuity Systems Inc./Qiagen; Redwood City, Calif.) as well as the genes encoding the group I mGluR signaling pathway described in Kelleher et al. [PMID: 22558107]. CNV calls were analyzed for overlap to known syndromic regions and GRM network genes. All syndromic aberrations detected by clinical cytogenetic laboratory testing were confirmed on corresponding SNP arrays.

Results: mGluR Network Copy Number Variations (CNVs) are Prevalent in Syndromic ASD Compared to Nonsyndromic ASD CNVs in the mGluR network genes were found in 74% of patients with syndromic ASD compared to 16% of patients with nonsyndromic ASD (p<0.001). Most of the mGluR CNV's in patients with syndromic ASD (75%) were included in larger clinically significant CNV's. As mGluR network genes are present in the 22q11.2 region (RANBP1) and on chromosome 21 (APP GRIK1 MX1 PCBP3 SETD4), patients with ASD in the presence of 22q11.2DS, 22q11.2DupS or Trisomy 21 accounted for 15 (33%) of the patients with Syndromic ASD+mGluR network changes. The remainder of observed cytogenetic changes had individual non-overlapping deletions or duplications. The analysis was repeated after exclusion of children with Trisomy 21, 22q11.2DS and 22q11.2DupS, (the syndromes in children in this study which have previously been associated with ASD). After their exclusion, the effect remained significant (p<0.001).

Autism Spectrum Disorder in 22q11.2 Deletion Syndrome is Associated with "Second Hit" in mGluR Pathway As a comparison cohort, data from children with 22q11.2 DS with ASD (n=25) and without ASD (n=50) who had completed high density microarray evaluation (either Affymetrix 6.0, Illumina 500K, and Illumina 610Q) and clinical developmental assessments (as enrolled through a parallel study, approved by the Children's Hospital of Philadelphia Institutional Review Board, IRB 07-005352) were examined for the presence of a second mGluR network hit outside of the 22q11.2 region. "Second hits", deletions of an mGluR network gene outside of the 22q11.2 region, were found in 20% (5/25) of patients with ASD and only 2% (1/50) without ASD (p<0.014).

Prior studies have demonstrated that abnormal signaling (either too much or too little) through mGluR5 could be the basis for abnormal neural development (and possibly ASD) in FXS and TS. Our data suggest that derangement of the mGluR network may be responsible for increased rates of ASD seen in cytogenetically distinct forms of syndromic ASD. mGluR network genes are found in the 22q11.2 region as well as on Chromosome 21, which may be involved in the increased prevalence of ASD in both Down Syndrome and 22q11.2 DS. However, all patients with Trisomy 21 or 22q11.2 DS harbor the change in the mGluR network suggesting a second hit outside of the region may be necessary for expression of the ASD phenotype.

Autism Spectrum Disorder in 22q11.2 Deletion Syndrome, 22q11.2 Duplication Syndrome, Thalidomide Embryopathy and Fetal Valproate Syndrome The 22q11.2 DS is the most common microdeletion syndrome in humans, occurring in 1 in 4,000 individuals. The typical deletion spans approximately 3 Mb and includes approximately 45 genes, causing a variety of medical and behavioral disorders. ASD occurs in approximately 20%, and psychosis in 25%. The 22q11.2DupS results in the same types of birth defects and medical comorbidities seen in 22q11.2 DS, but at a lower rate (among over 60 patients in our clinical cohort). There are no cases of psychosis in 22q11DupS in the literature.sup.29 or our cohort. Among our cases with documentation of developmental evaluation after the age of 4, the prevalence of ASD is 27%, which is slightly higher than the rate in children with 22q11.2DS.

Thalidomide exposure during pregnancy causes a variety of birth defects that have all been reported in 22q11.2DS, including some that are extremely rare (e.g. phocomelia, radial ray defects). Miller and Stromland reported an elevated risk of ASD following exposure to thalidomide during early embryogenesis. This study included prospective evaluation by a psychiatrist was done for adults who had been exposed to thalidomide during pregnancy and evaluation by a physician to document birth defects and associated features. All cases of ASD following thalidomide exposure had ear anomalies, suggesting exposure between days 24-28 post-fertilization. Among individuals exposed at this time, there was a 27% rate of ASD. Replications of this study in additional cohorts of children have not been possible because the use of thalidomide in pregnant women was widely restricted in the 1960's; therefore, additional cases are not available. Though several mechanisms for the cause of many of the birth defects in thalidomide embryopathy have been proposed, animal studies of the teratogenic effects of thalidomide have been limited due to significant species differences. One of the reasons thalidomide was used widely in the 1960's was because of a lack of teratogenicity in animals at levels that are highly teratogenic in humans. This has resulted in significant limitation in the ability of researchers to determine the teratogenic mechanism of thalidomide, as studies have taken place in animals for which thalidomide is not particularly teratogenic, or using dosages which are much higher than that used in humans. Recent changes in legislation have allowed for a study to be completed in human embryonic stem cells—the first of its kind to use human cells and dosages which would have been analogous to that experienced by women taking thalidomide in the 1950's and 1960's.sup.30. This study, conducted by Meganathan and colleages (2012) proposed that the teratogenic effects of thalidomide may be mediated through RANBP1. Valproic acid (VPA) is widely used as an anticonvulsant, mood stabilizer, and to prevent migraine headaches. Exposure to VPA during pregnancy causes an increased rate of several birth defects, all of which have been reported in 22q11.2DS, and most of which have been seen in Thalidomide Embryopathy. The comparison of all birth defects seen in 22q11.2 DS to the exposures syndromes was not made because 22q11.2 DS includes deletion of dozens of additional genes that we do not propose to be affected in Thalidomide Embryopathy or Fetal Valproate Syndrome. In addition to structural defects, children exposed to VPA in utero have an elevated risk of developing ASD. Rodent models of autism have used prenatal exposure to VPA to reproduce some of the neuroanatomic features of autism and abnormal behavior. Due to its action as a Histone Deacetylase Inhibitor, VPA affects expression of many genes. Based on homology, decreased expression of RanBP1 mRNA is predicted in VPA-treated rats. Moreover, a recent study showed reversal of atypical behaviors in VPA-exposed mice with treatment with an mGluR antagonist.

Conclusions

Derangement of genes in the mGluR network are found at a high rate in patients with different forms of Syndromic ASD, including 22q11.2DS, 22q11.2DupS, Trisomy 21 and a large number of other seemingly-unrelated chromosomal alterations. Moreover, among children with 22q11.2DS, the presence of a "second hit" in the mGluR network was identified in 20% of children with ASD, and only 2% of those without ASD (p<0.014). Significantly, four children, all with autism phenotype, had a small deletion in the vicinity of the RANBP1 gene. While the expression level of RANBP1 was not affected in one individual available for testing (data not shown), these atypical deletions could impact gene function with resulting dysregulation of the RANBP1 protein.

Taken together, these data implicate dysregulation of the mGluR network as a likely permissive factor that increases the propensity to develop an ASD, including syndromic ASD, and ASD in individuals with 22q11.2 Deletion or Duplication Syndrome, Fetal Valproate Syndrome and Thalidomide Embryopathy. The striking increase in prevalence of ASD with a CNV affecting a second gene in the network suggests perturbations of mGluR signaling at multiple points is likely.

CNVs in the genes recited in FIG. 15 are sensitive and specific biomarkers for selecting and treating ASD, syndromic ASD, and ASD in individuals with 22q11.2 Deletion or Duplication Syndrome, Fetal Valproate Syndrome and Thalidomide Embryopathy. Furthermore, the present inventors have identified drug candidates that specifically activate the mGluRs, potentially restoring normal neurophysiology in patients with mutations in any of the mGluR network genes, as shown in FIG. 15.

For example, compounds which may be administered in implementing the test and treat paradigm described herein include the piracetam family of nootropic agents, as described in F. Gualtieri et al., Curr. Phann. Des., 8: 125-38 (2002). More preferably, the treating agent is a pyroglutamide. Details regarding the preparation and formulation of pyroglutamides, which may be used in the practice of this invention, are provided in U.S. Pat. No. 5,102,882 to Kimura et al. A particularly preferred agent for the treatment of ASD in patients determined to have one or more of the CNVs indicative as set forth in FIG. 15, is (+)-5-oxo-Dprolinepiperidinamide monohydrate (NS-105).

Therefore, in one embodiment, methods for treating an ASD, syndromic ASD, and ASD in patients with 22q11.2 Deletion or Duplication Syndrome, Fetal Valproate Syndrome or Thalidomide Embryopathy are encompassed comprising administering NS-105 to a patient having at least one CNV in an GRM/mGluR network gene selected from the group consisting of ACAT1, ACAT2, ACP1, ACTR2, ADCY1, ADD1, ADRA2C, ADRBK1, AGAP2, ALDOA, APTX, ARHGAP24, ARL15, BDKRB1, BDKRB2, C1orf116, C4orf3, C7orf25, CA8, CACNA1B, CALB2, CALM1, CAMK2B, CHP, CHRM3, CNPY2, CNR1, COPB2, DCN, DHCR7, DISC1, DSTN, ECHS1, EGFR, ERBB2, ERP44, F2RL2, FKBP3, FURIN, GLP1R, GLP2R, GNA15, GNAI1, GNAI2, GNAI3, GNAO1, GNAQ, GNB2L1, GRB2, GRB7, GRIK1, GRM1, GRM3, GRM5, GRM7, GRM8, GSN, HNRNPA3, HOMER1, HOMER3, HTT, IMPDH2, IQGAP2, ITGB7, ITPR1, LAMA4, LRP2BP, LYAR, LYN, MAP4, MAPK1, MTHFD1, MTNR1A, MX1, MYO6, NAA15, NCK1, NPY2R, PCBP1, PCBP3, PCDHA4, PDE1C, PICK1, PIK3CA, PLA2G7, PLCB1, PRDX1, PRKCA, PRPSAP1, PSMC1, PSMD1, PSMD13, PSME1, PXN, RAB2A, RANBP1, RAP2A, RCC1, RGS12, RPA2, RPN2, RUVBL2, RYR2, S100A6, SACS, SDC3, SERPINB9, SLC6A3, SNRPB2, SRC, STRAP, STX12, SYK, TCP1, TEAD3, TFAM, TJP1, TRAF2, TUBA1A, TUBA3C, TXN, UBQLN4, VHL, and YWHAQ.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method of treating autism spectrum disorder (ASD) in a human patient comprising
   a) obtaining genotyping data indicating that the patient has at least one CNV which is a duplication CNV of chromosomal region chr22:20107729-20117344,
   b) correlating the presence of said CNV identified in step a) with diagnosis of ASD in the patient, and
   c) administering a therapeutically effective amount of fasoracetam to the patient, thereby treating ASD in the patient.

2. The method of claim 1, wherein the ASD is syndromic.

3. The method of claim 1, wherein the patient has ASD and 22q11.2 Deletion or Duplication Syndrome, Fetal Valproate Syndrome or Thalidomide Embryopathy.

4. The method of claim 1, further comprising detection of at least one additional CNV, wherein the additional CNV is selected from a duplication in ACAT1, a deletion in ACAT2, a duplication in ACP1, a duplication in ACTR2, a deletion in ADCY1, a duplication in ADD1, a duplication in ADRA2C, a deletion in ADRBK1, a duplication in AGAP2, a deletion in ALDOA, a duplication in APTX, a deletion in ARHGAP24, a deletion in ARL15, a duplication in BDKRB1, a duplication in BDKRB2, a deletion in C1orf116, a deletion in C4orf3, a duplication in C7orf25, a duplication in CA8, a duplication in CACNA1B, a duplication in CALB2, a duplication in CALM1, a deletion in CAMK2B, a deletion in CHP, a duplication in CHRM3, a duplication in CNPY2, a duplication in CNR1, a deletion in COPB2, a deletion in DCN, a duplication in DHCR7, a deletion in DISC1, a duplication in DSTN, a duplication in ECHS1, a deletion in EGFR, a duplication in ERBB2, a deletion in ERP44, a deletion in F2RL2, a deletion in FKBP3, a duplication in FURIN, a deletion in GLP1R, a duplication in GLP2R, a duplication in GNA15, a duplication in GNAI1, a deletion in GNAI2, a deletion in GNAI3, a deletion in GNAO1, a duplication in GNAQ, a duplication in GNB2L1, a deletion in GRB2, a duplication in GRB7, a deletion in GRIK1, a deletion in GRM1, a deletion in GRM3, a deletion in GRM5, a deletion in GRM7, a deletion in GRM8, a duplication in GSN, a deletion in HNRNPA3, a deletion in HOMER1, a duplication in HOMER3, a duplication in HTT, a deletion in IMPDH2, a deletion in IQGAP2, a duplication in ITGB7, a deletion in ITPR1, a duplication in LAMA4, a deletion in LRP2BP, a duplication in LYAR, a deletion in LYN, a duplication in MAP4, a deletion in MAPK1, a deletion in MTHFD1, a duplication in MTNR1A, a deletion in MX1, a deletion in MYO6, a deletion in NAA15, a duplication in NCK1, a deletion in NPY2R, a duplication in PCBP1, a duplication in PCBP3, a deletion in PCDHA4, a deletion in PDE1C, a deletion in PICK1, a deletion in PIK3CA, a deletion in PLA2G7, a deletion in PLCB1, a deletion in PRDX1, a deletion in PRKCA, a deletion in PRPSAP1, a duplication in PSMC1, a deletion in PSMD1, a deletion in PSMD13, a duplication in PSME1, a duplication in PXN, a deletion in RAB2A, a duplication in RANBP1, a deletion in RAP2A, a deletion in RCC1, a duplication in RGS12, a deletion in RPA2, a deletion in RPN2, a duplication in RUVBL2, a deletion in RYR2, a deletion in S100A6, a deletion in SACS, a duplication in SDC3, a deletion in SERPINB9, a duplication in SLC6A3, a duplication in SNRPB2, a deletion in SRC, a deletion in STRAP, a deletion in STX12, a duplication in SYK, a deletion in TCP1, a duplication in TEAD3, a deletion in TFAM, a deletion in TJP1, a duplication in TRAF2, a deletion in TUBA1A, a duplication in TUBA3C, a duplication in TXN, a deletion in UBQLN4, a duplication in VHL, and a deletion in YWHAQ.

5. The method of claim 1, wherein the patient has been diagnosed with one or more of pervasive developmental disorder, autism, Asperger's syndrome, childhood disintegrative disorder, Rett's disorder, and social (pragmatic) communication disorder (SCD).

* * * * *